United States Patent
Sørensen

(10) Patent No.: US 11,945,144 B2
(45) Date of Patent: Apr. 2, 2024

(54) TIP PART ASSEMBLY FOR AN ENDOSCOPE

(71) Applicant: Ambu A/S, Ballerup (DK)

(72) Inventor: Morten Sørensen, Ballerup (DK)

(73) Assignee: AMBU A/S, Ballerup (DK)

( * ) Notice: Subject to any disclaimer, the term of this patent is extended or adjusted under 35 U.S.C. 154(b) by 332 days.

(21) Appl. No.: 17/013,445

(22) Filed: Sep. 4, 2020

(65) Prior Publication Data

US 2021/0068640 A1 Mar. 11, 2021

(30) Foreign Application Priority Data

Sep. 6, 2019 (EP) .................................... 19195989
Sep. 6, 2019 (EP) .................................... 19195995

(Continued)

(51) Int. Cl.
*B29C 45/14* (2006.01)
*A61B 1/00* (2006.01)
(Continued)

(52) U.S. Cl.
CPC .... *B29C 45/14467* (2013.01); *A61B 1/00094* (2013.01); *A61B 1/00105* (2013.01);
(Continued)

(58) Field of Classification Search
CPC .......... B29C 45/14467; A61B 1/00105; A61B 1/0011; A61B 1/00124; A61B 1/018;
(Continued)

(56) References Cited

U.S. PATENT DOCUMENTS 4,779,130 A 10/1988 Yabe
5,609,561 A 3/1997 Uehara et al.
(Continued)

FOREIGN PATENT DOCUMENTS

CN 201499375 U 6/2010
CN 104995907 B 5/2019
(Continued)

OTHER PUBLICATIONS

Extended search report in European Application No. 1919 5995, dated Dec. 13, 2019.
Extended search report in European Application No. 1919 5996, dated Dec. 13, 2019.
Extended search report in European Application No. 1919 5989, dated Jan. 3, 2020.
Search Report issued by the European Patent Office, dated Dec. 2, 2019, for European Application No. EP19195998, 11 pages.
(Continued)

*Primary Examiner* — Anh Tuan T Nguyen
*Assistant Examiner* — Shankar Raj Ghimire
(74) *Attorney, Agent, or Firm* — Faegre Drinker Biddle & Reath LLP

(57) ABSTRACT

A tip part assembly for an endoscope, a method for assembling the tip part assembly, and an endoscope including the tip part assembly. The tip part assembly includes a flexible printed circuit having connection points, a camera module including a connection surface comprising connection points arranged in a first connection point pattern for electrical communication with the connection points of the flexible printed circuit, and a converter circuit board including a first surface including connection points arranged substantially in the first connection point pattern and a second surface including connection points arranged in a second connection point pattern being different than the first connection point pattern, wherein the first surface connection points are connected to the connection surface connection points, and wherein the second surface connection points are connected to the connection points of the flexible printed circuit.

19 Claims, 7 Drawing Sheets

(30) Foreign Application Priority Data

Sep. 6, 2019 (EP) .................................... 19195996
Sep. 6, 2019 (EP) .................................... 19195998

(51) Int. Cl.

| | | |
|---|---|---|
| A61B 1/005 | (2006.01) | |
| A61B 1/015 | (2006.01) | |
| A61B 1/018 | (2006.01) | |
| A61B 1/05 | (2006.01) | |
| A61B 1/06 | (2006.01) | |
| A61B 1/07 | (2006.01) | |
| A61B 1/307 | (2006.01) | |
| B29K 105/00 | (2006.01) | |
| B29L 31/00 | (2006.01) | |

(52) U.S. Cl.
CPC ........ *A61B 1/0011* (2013.01); *A61B 1/00124* (2013.01); *A61B 1/009* (2022.02); *A61B 1/015* (2013.01); *A61B 1/018* (2013.01); *A61B 1/051* (2013.01); *A61B 1/0684* (2013.01); *A61B 1/07* (2013.01); *A61B 1/307* (2013.01); *B29K 2105/0097* (2013.01); *B29L 2031/7546* (2013.01)

(58) Field of Classification Search
CPC ......... A61B 1/051; A61B 1/0684; A61B 1/07; A61B 1/05
See application file for complete search history.

(56) References Cited

U.S. PATENT DOCUMENTS

| | | | |
|---|---|---|---|
| 5,951,464 A | 9/1999 | Takahashi et al. | |
| 7,662,094 B2 | 2/2010 | Iddan | |
| 7,833,151 B2* | 11/2010 | Khait | A61B 1/041 |
| | | | 600/109 |
| 8,414,480 B2 | 4/2013 | Kendale et al. | |
| 8,485,966 B2 | 7/2013 | Robertson | |
| 9,125,582 B2 | 9/2015 | Petersen | |
| 9,158,037 B2 | 10/2015 | Otsuka et al. | |
| 9,622,649 B2 | 4/2017 | Lin | |
| 9,814,371 B2 | 11/2017 | Segi et al. | |
| 9,866,738 B2* | 1/2018 | Kojima | A61B 1/00124 |
| 10,025,088 B2* | 7/2018 | Handte | H04N 5/2251 |
| 10,188,275 B2 | 1/2019 | Sonnenschein et al. | |
| 2002/0193663 A1 | 12/2002 | Matsuura | |
| 2003/0113642 A1 | 6/2003 | Kami et al. | |
| 2004/0027459 A1 | 2/2004 | Segawa et al. | |
| 2004/0242963 A1 | 12/2004 | Matsumoto et al. | |
| 2005/0143659 A1* | 6/2005 | Saiga | A61B 1/00124 |
| | | | 600/463 |
| 2005/0222499 A1 | 10/2005 | Banik et al. | |
| 2005/0277340 A1 | 12/2005 | Gordon et al. | |
| 2006/0264704 A1* | 11/2006 | Fujimori | A61B 1/04 |
| | | | 600/101 |
| 2007/0027360 A1 | 2/2007 | Mitsuya | |
| 2007/0249907 A1* | 10/2007 | Boulais | A61B 5/064 |
| | | | 600/179 |
| 2008/0132760 A1 | 6/2008 | Takeuchi | |
| 2008/0242935 A1 | 10/2008 | Inoue | |
| 2008/0266441 A1* | 10/2008 | Ichimura | H04N 5/2254 |
| | | | 348/340 |
| 2008/0312504 A1 | 12/2008 | Kimoto | A61B 5/0031 |
| | | | 600/118 |
| 2009/0012358 A1* | 1/2009 | Ichihashi | A61B 1/00108 |
| | | | 600/110 |
| 2009/0259101 A1* | 10/2009 | Unsai | A61B 1/05 |
| | | | 600/110 |
| 2009/0260553 A1 | 10/2009 | Skovbo | |
| 2009/0295913 A1 | 12/2009 | Sato et al. | |
| 2010/0016667 A1* | 1/2010 | Segawa | A61B 1/00105 |
| | | | 600/118 |
| 2010/0185052 A1* | 7/2010 | Chang | H04N 5/2253 |
| | | | 600/112 |
| 2011/0118549 A1 | 5/2011 | Han | |
| 2011/0288372 A1 | 11/2011 | Petersen | |
| 2012/0197081 A1* | 8/2012 | Kimura | A61B 1/00124 |
| | | | 600/110 |
| 2012/0220825 A1* | 8/2012 | Kimura | A61B 1/00124 |
| | | | 600/109 |
| 2012/0229615 A1* | 9/2012 | Kirma | A61B 1/05 |
| | | | 348/E7.085 |
| 2013/0041223 A1* | 2/2013 | Kato | A61B 1/0051 |
| | | | 600/121 |
| 2013/0060083 A1 | 3/2013 | Oku | |
| 2013/0150667 A1 | 6/2013 | Mitamura et al. | |
| 2013/0172678 A1* | 7/2013 | Kennedy, II | A61B 1/05 |
| | | | 600/109 |
| 2013/0175720 A1 | 7/2013 | Otsuka et al. | |
| 2013/0271588 A1* | 10/2013 | Kirma | A61B 1/05 |
| | | | 348/76 |
| 2014/0073853 A1 | 3/2014 | Swisher et al. | |
| 2014/0100421 A1 | 4/2014 | Dejima et al. | |
| 2014/0142384 A1 | 5/2014 | Chung et al. | |
| 2014/0210976 A1* | 7/2014 | Lin | G02B 23/2476 |
| | | | 348/68 |
| 2014/0330081 A1 | 11/2014 | Shunichi | |
| 2015/0005580 A1 | 1/2015 | Petersen | |
| 2015/0062316 A1 | 3/2015 | Haraguchi et al. | |
| 2015/0094534 A1 | 4/2015 | Yamada | |
| 2015/0148603 A1 | 5/2015 | Holste | |
| 2015/0312457 A1* | 10/2015 | Kojima | H05K 1/021 |
| | | | 29/840 |
| 2015/0358518 A1* | 12/2015 | Ishii | A61B 1/051 |
| | | | 600/109 |
| 2015/0378144 A1* | 12/2015 | Handte | H01L 27/14601 |
| | | | 250/208.1 |
| 2016/0029879 A1* | 2/2016 | Ishikawa | A61B 1/00124 |
| | | | 600/110 |
| 2016/0051222 A1 | 2/2016 | Imahashi | |
| 2016/0209637 A1* | 7/2016 | Fujimori | G02B 23/2423 |
| 2016/0235629 A1 | 8/2016 | Allyn et al. | |
| 2016/0287060 A1 | 10/2016 | Usuda et al. | |
| 2016/0313552 A1* | 10/2016 | Tomatsu | A61B 1/00013 |
| 2017/0108691 A1* | 4/2017 | Kitano | A61B 1/00096 |
| 2017/0108692 A1* | 4/2017 | Kitano | G02B 23/2484 |
| 2017/0123200 A1* | 5/2017 | Suyama | A61B 1/051 |
| 2017/0245734 A1 | 8/2017 | Kaneko | |
| 2017/0251914 A1* | 9/2017 | Kitano | H04N 5/2257 |
| 2017/0325663 A1 | 11/2017 | Levy et al. | |
| 2018/0070803 A1* | 3/2018 | Mikami | G02B 23/2423 |
| 2018/0153381 A1 | 6/2018 | Wei et al. | |
| 2018/0160893 A1 | 6/2018 | Truckai et al. | |
| 2018/0168041 A1 | 6/2018 | Govrin et al. | |
| 2018/0242822 A1 | 8/2018 | Hamazaki | |
| 2018/0317756 A1* | 11/2018 | Unsai | H04N 5/2254 |
| 2019/0150711 A1* | 5/2019 | Chiu | A61B 1/00071 |
| 2019/0191968 A1 | 6/2019 | Tsumaru | |
| 2019/0282070 A1 | 9/2019 | Vilhelmsen et al. | |
| 2020/0163535 A1* | 5/2020 | Sekido | H01L 24/92 |
| 2020/0178766 A1 | 6/2020 | Ichihara | |
| 2020/0192078 A1* | 6/2020 | Spring | H05K 1/0298 |
| 2020/0225461 A1* | 7/2020 | Aizenfeld | A61B 1/051 |
| 2020/0288953 A1* | 9/2020 | Sørensen | G02B 23/2484 |
| 2020/0297193 A1 | 9/2020 | Takahashi et al. | |
| 2021/0068634 A1 | 3/2021 | Sørensen | |
| 2021/0068640 A1* | 3/2021 | Sørensen | A61B 1/018 |
| 2021/0068641 A1 | 3/2021 | Sørensen | |
| 2021/0068642 A1* | 3/2021 | Sørensen | A61B 1/00105 |
| 2021/0105386 A1 | 4/2021 | Satake | |
| 2021/0153729 A1* | 5/2021 | Kirma | H04N 5/2258 |
| 2022/0061630 A1 | 3/2022 | Yan et al. | |

FOREIGN PATENT DOCUMENTS

| | | | |
|---|---|---|---|
| DE | 102010034623 A1 | 2/2012 | |
| EP | 0306723 B1 | 3/1989 | |
| EP | 0754429 B1 | 9/2004 | |
| EP | 2110069 B1 | 3/2011 | |
| EP | 2594307 A1 | 5/2013 | |

(56) References Cited

FOREIGN PATENT DOCUMENTS

| | | | |
|---|---|---|---|
| EP | 2692277 A1 | 2/2014 | |
| EP | 2913850 A1 | 9/2015 | |
| EP | 2692227 B1 | 8/2018 | |
| EP | 2677736 B1 | 11/2018 | |
| JP | 2004008638 A | 1/2004 | |
| JP | 2008118568 A | 5/2008 | |
| JP | 2010005277 A | 1/2010 | |
| JP | 2011200397 A | 10/2011 | |
| JP | 2011200399 A | 10/2011 | |
| JP | 2011217887 A | 11/2011 | |
| JP | 2012-201065 A | 10/2012 | |
| JP | 2015002805 A | 1/2015 | |
| JP | 2015058118 A | 3/2015 | |
| JP | 5977892 B1 * | 8/2016 | ......... A61B 1/00018 |
| JP | 2016221316 A | 12/2016 | |
| JP | 2017074207 A | 4/2017 | |
| JP | 2018-093907 A | 6/2018 | |
| WO | 01/10295 A1 | 2/2001 | |
| WO | 2008/023965 A1 | 2/2008 | |
| WO | 2010066790 A1 | 6/2010 | |
| WO | 2014203604 A1 | 12/2014 | |
| WO | 2018/022402 A1 | 2/2018 | |
| WO | 2018/022418 A2 | 2/2018 | |
| WO | 2019138462 A1 | 7/2019 | |

OTHER PUBLICATIONS

Extended search report in European Application No. 2019 1424, dated Feb. 1, 2021.
Examination Report issued in EP 19 195 998.0, dated Jun. 28, 2023, 5 pages.
Examination Report issued in EP 20 191 424.9, dated Jul. 5, 2023, 5 pages.

* cited by examiner

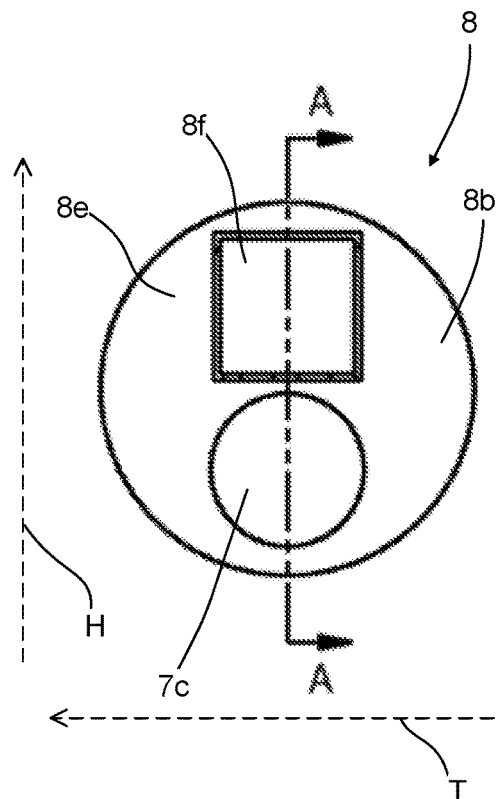
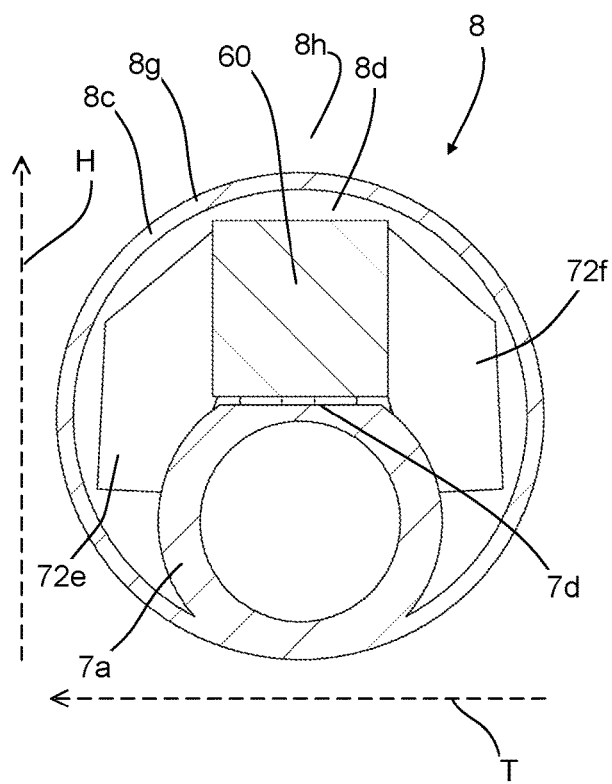
FIG. 4a
FIG. 4b
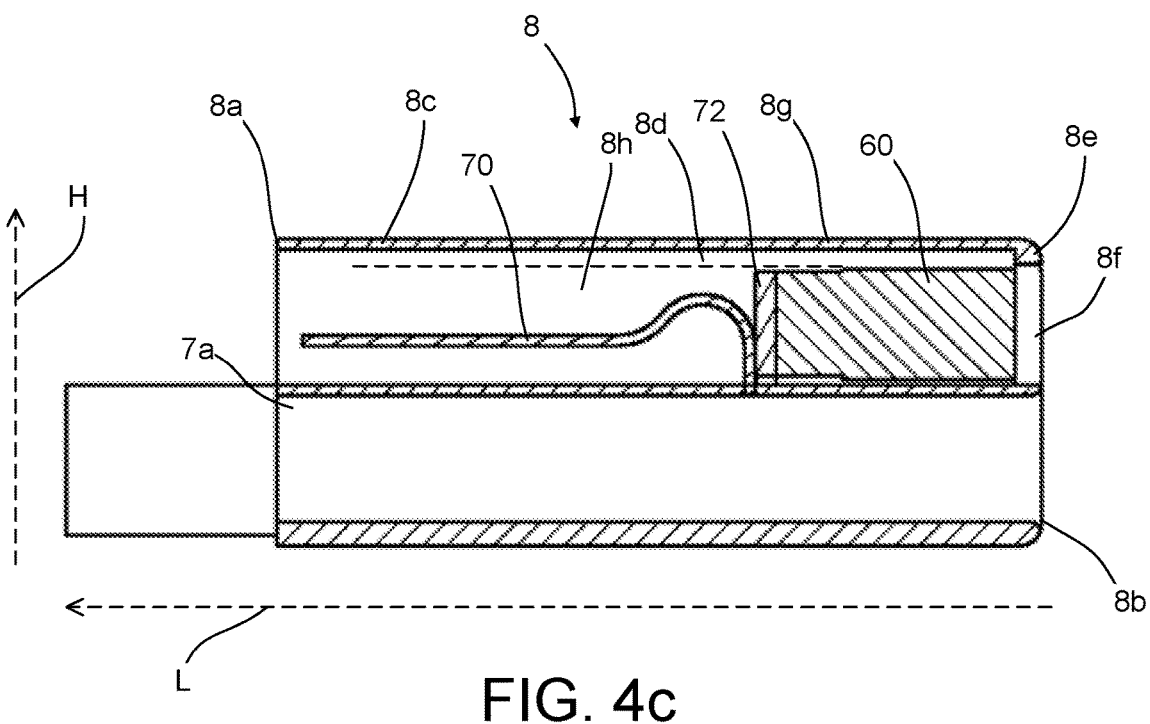
FIG. 4c

TIP PART ASSEMBLY FOR AN ENDOSCOPE

CROSS-REFERENCE TO RELATED PATENTS

The present application claims priority from, and the benefit of, European Patent Application Nos. 19195989.9, 19195995.6, 19195996.4, and 19195998.0, filed Sep. 6, 2019, which applications are incorporated by reference herein in their entirety.

Commonly owned U.S. patent application Ser. Nos. 17/013,519, 17/013,488, and 17/013,463, filed concurrently with the present application, claim priority from European Patent Application Nos. 19195989.9, 19195995.6, 19195996.4, and 19195998.0, and are incorporated by reference herein in their entirety.

TECHNICAL FIELD

The present disclosure relates to endoscopes and more specifically to a tip part assembly for an endoscope.

BACKGROUND

Endoscopes are well known for visually inspecting places that are difficult to access, such as human body cavities. Typically, the endoscope comprises an elongated insertion tube with a handle at the proximal end, as seen from the operator, and visual inspection means, such as a built-in camera, at the distal end of the elongated insertion tube. This definition of the terms distal and proximal, i.e. proximal being the end closest to the operator and distal being the end remote from the operator, as used herein for endoscopes in general, is adhered to in the present specification.

As the name indicates, endoscopes are used for seeing inside things, such as lungs or other human body cavities of a patient. Modern endoscopes are therefore typically equipped with a light source and a vision receptor including a vision sensor, such as a camera or an image sensor. Provided that sufficient light is present, it is possible for the operator to see where the endoscope is steered and to set the target of interest once the tip has been advanced thereto. This therefore normally requires illumination of the area in front of the light source, such as a light emitting diode, LED, or an optical fibre, may provide illumination.

Electrical wiring for the camera and other electronics, such as LED lighting accommodated in the tip part assembly at the distal end, run along the inside of the elongated insertion tube from the handle to the tip part assembly. Instead of using cameras, endoscopes may also be fibre-optic, in which case the optical fibres run along the inside of the elongated insertion tube to the tip part assembly. For some applications, a working or suction channel may run along the inside of the insertion tube from the handle to the tip part assembly, e.g. allowing liquid to be removed from the body cavity or allowing for insertion of surgical instruments or the like, into the body cavity. The suction channel may be connected to a suction connector, typically positioned at a handle at the proximal end of the insertion tube. For other applications, the working or suction channel may be omitted.

In order to be able to manoeuvre the endoscope inside the body cavity, the distal end of the endoscope may comprise a bending section with increased flexibility, e.g. an articulated tip part assembly allowing the operator to bend this section. Typically, this is done by tensioning or slacking steering wires also running along the inside of the elongated insertion tube from the articulated tip part assembly to a control mechanism of the handle.

A general desire in the field of endoscopy is to electrically insulate the insertion tube, and thus especially the tip part assembly, from the outside, so as to mitigate the risk of an insulation breakdown and a resulting excessive leakage current.

Another general desire in the field of endoscopy is to provide a tip part assembly which is liquid-sealed, so as to mitigate liquid ingress into the tip part assembly, and specifically into any electrical or optical components of the tip part assembly.

For some types of endoscopes, such as urethroscope, there is a desire to provide the tip part assembly of the endoscope with a smaller diameter or cross sectional extent, especially where the tip part assembly is to be inserted into narrower body cavities. In very narrow body cavities, even a reduction of 1 mm or less in the cross-sectional extent of a tip part assembly can have a noticeable effect on the comfort of the patient and may even make it possible to reach body areas not otherwise accessible. Providing a small size of the tip part assembly can especially be a challenge in cases where the endoscope comprises both a camera and a working channel extending through the tip part assembly since the camera and working channel are positioned one above the other within the tip part assembly, which takes up space in a radial direction of the tip part assembly. In some prior art tip part assembly assemblies, a flexible printed circuit (FPC) and a camera module are included. The FPC is connected to a connection surface proximally of or at a rear side of the camera module. The camera module comprises an image sensor and a lens stack positioned distally or in front of the image sensor. Where a working channel is included as well, the camera module is positioned above the working channel within a housing with a typically circular-cylindrical circumferential outer surface. The FPC lies side-by-side with and is connected to the connection surface of the camera module. From this connection, the FPC extends upwardly, i.e. away from the working channel, into a fold towards a proximal end of the housing. Further towards or beyond a proximal end of the housing where there is room proximally of or behind the connection surface of the camera module, the FPC includes electrical components for the camera module and potentially any LEDs.

It is therefore desirable to provide a tip part assembly with a small outer diameter for an endoscope, such as a urethroscope, having electrically insulating properties and with a mechanically stable printed circuit.

On this background it is desirable to provide an improved tip part assembly for an endoscope, which at least mitigates some of the abovementioned drawbacks.

SUMMARY

A first aspect of this disclosure relates to a tip part assembly for an endoscope, comprising: a flexible printed circuit having two or more connection points, a camera module comprising a connection surface comprising two or more connection points for electrical communication of the camera module with the connection points of the flexible printed circuit, the connection points of the connection surface being arranged in a first connection point pattern, and a converter circuit board comprising a first surface and a second surface opposite the first surface, the first surface of the converter circuit board comprising connection points similarly arranged substantially in the first connection point pattern so that positions of the first surface connection points correspond to the connection surface connection points, the second surface of the converter circuit board comprising connection points arranged in a second connection point pattern, the second connection point pattern being different from the first connection point pattern, wherein the first surface connection points are connected to the connection surface connection points so that positions of the first surface connection points correspond to associated positions of the connection surface connection points, and wherein the second surface connection points are connected to the connection points of the flexible printed circuit.

It has been realized that in the above mentioned prior art tip part assemblies including a camera module and a FPC, the location of the fold of the FPC may be determined by the location of the camera module and its connection points. According to the present disclosure, the converter circuit board may, however, allow for the FPC to be connected to the camera module via the converter circuit board and thereby at another position, such as offset in a direction parallel to and away from a geometric centre of the camera module connection surface. So, instead of folding the FPC such that substantially an entire fold is located in a top volume of the housing as in the prior art, which means that the top volume of a housing above a top level of the camera module must provide room for the FPC fold, according to the present disclosure, the substantially entire FPC fold or the entire FPC fold may be arranged in a volume behind the camera module, i.e. proximally of the camera module, when seen in a proximal-distal direction of the endoscope.

This means that the mentioned top volume of the housing is not necessary and can be dispensed with or be reduced. This again means that the extent of the housing in a height direction can be reduced. This is due to the height direction typically being decisive for the necessary diameter or cross-sectional extent of the housing since there is typically more room at a lateral side of the camera module.

Therefore, the diameter or the cross-sectional extent of the housing and thus the tip part assembly can therefore be reduced. This reduction can be from about 0.1 and up to 1 mm or more. Hereby, a patient's comfort during an endoscopy procedure may be improved, and the tip part assembly may even provide access to body areas not otherwise accessible. It has been shown that an outer diameter of the circumferential wall of the tip part assembly, where this further comprises a working channel, of less than 3 mm or even smaller may be achieved.

The term "fold" as used herein may alternatively be denoted "bend". Similarly, the term "folding" may alternatively be denoted "bending".

In such a tip part assembly, a risk of electrical conduction from the electronics inside a housing, such as the FPC, and through the housing to the patient may be mitigated in use, as the FPC may be positioned with at a distance from the housing. The material thickness necessary for the housing material to provide sufficient electrically insulating properties, which may impact the tip part assembly cross-section or diameter, may be reduced to be generally of a size suitable for certain types of endoscopes, such as urethroscopes. Another advantage may be that the risk that the FPC at least partly breaks when bending and/or folding it or that the fold of the FPC gets in physical contact with the housing and at least partly breaks due to wear may be mitigated.

An outer diameter of a circumscribed circle in a cross-section of the tip part assembly may be reduced compared to a tip part assembly with an, e.g. in a height direction, upwardly extending FPC fold arranged in the a top volume. Thus, the inner and outer cross-section and/or diameter of a housing, where such is provided, may be reduced, in turn allowing for a small tip part assembly. In the tip part assembly according to the present disclosure, an FPC fold may alternatively or additionally extend downwards in the height direction.

The term "endoscope" may be defined as a device suitable for examination of natural and/or artificial body openings, e.g. for exploration of a lung cavity. Additionally, or alternatively, the term "endoscope" may be defined as a medical device.

Throughout this specification, the term camera assembly may be defined as a sub-assembly of the tip part assembly. The camera assembly may comprise the camera module, the converter circuit board and the flexible printed circuit.

In this specification, a proximal-distal direction may be defined as an axis extending along the parts of the insertion tube of the endoscope. Adhering to the definition of the terms distal and proximal, i.e. proximal being the end closest to the operator and distal being the end remote from the operator. The proximal-distal direction is not necessarily straight, for instance, if the insertion tube is bent, then the proximal-distal direction follows the curvature of the insertion tube. The proximal-distal direction may for instance be a centre line of the insertion tube.

The distal end of the tip part assembly may form a distal end of the endoscope.

The tip part assembly may have a proximal end for being connected to other parts of the endoscope and a distal end positioned oppositely from the proximal end for forming a distal end of the endoscope. A longitudinal direction may extend from the proximal end towards the distal end of the tip part assembly. A height direction may extend transversely to the longitudinal direction. A lateral direction may extend transversely to the longitudinal and height directions. Angles between these three directions may be right. The lateral direction may also be denoted as a width direction.

An exterior flexible sleeve may be provided to extent around at least part of the tip part assembly, potentially of a housing thereof.

Flexible printed circuits (FPCs) or flex prints are well-known electronic items that can be manufactured by technologies such as flexible electronics or flex circuits. The FPC may, throughout this specification, be a single- or double-sided flexible circuit or a rigid-flex circuit and may comprise one or more layers of conductive material and two or more layers of insulating material, and/or may be a flexible flat cable having one or more conductors. In some embodiments, the FPC may be connected to a second flexible printed circuit and/or to a printed circuit board (PCB), e.g. comprising one or more copper layers and one or more layers of insulating materials, such as layers of a FR-4 (flame retardant) composite material.

FPCs can be considered a type of PCBs in which the carrier medium is more flexible and less elastic than in traditional, rigid PCBs, allowing the FPC to be folded and to flex during use. In FPCs, electronic devices are typically mounted on flexible plastic carrier materials or substrates. Flex circuits can be printed circuits on polyester. Other processes and materials for manufacture of FPCs are also known in the art.

The "converter circuit board" may alternatively be denoted the "adapter circuit board". The converter circuit board may be a potentially rigid printed circuit board (PCB), such as a PCB comprising one, two, or more layers of copper and one or more layers of insulating materials, such as FR-4, or a flexible printed circuit (FPC) as described above. It should be understood that the term "printed" is used generically to denote placement of copper layers or tracings on a board and does not limit a PCB to the particular method of placing the copper layers or tracings on the board. Similarly, while the board can be rigid, it can also be semi-rigid or flexible.

The converter circuit board may extend substantially in a plane or in a plane and/or may be larger than the connection surface of the camera module. The converter circuit board may have a substantially identical or identical extent in a height direction as the connection surface and/or may have a longer extent in a width direction than the connection surface.

Each of the second surface connection points may be in electrical connection with a respective one of the first surface connection points. The electrical connection may be a low resistance connection and/or may be provided by routing of and/or in the converter circuit board.

The first surface connection points may be arranged in the first connection point pattern.

The term "connection point" as used herein may alternatively be denoted "connection" and is not intended to be limited to being points in a mathematical sense, but may rather extend over an area of some size.

One or more connection points may be provided as a connection pin and may include a solder material. Alternatively, or additionally, one or more connection points may be provided as pads, such as solder pads, which may have an electrically conducting material on a surface thereof, or may be provided as solder balls. Where a plurality of connection points is provided as solder balls, the connection points may form ball grid array (BGA).

The connection surface connection points of the camera module may be provided as connection pins including a solder material and protruding from the connection surface. The connection surface connection pins may have a substantially circular or circular cross-section when seen in a direction perpendicular to the connection surface. Solder material may be applied and may be arranged in a substantially hemisphere shape or hemisphere shape on a connection surface connection point and/or connection pin. One or more connection points of the converter circuit board and/or of the FPC may be provided as solder pads for soldering and/or anisotropic conductive film (ACF) bonding to a respective other connection point.

A connection point pattern may substantially have the shape of or have the shape of a straight line, a circle, an ellipse, and/or a polygon, such as a triangle, a rectangle, a parallelogram, a trapezoid, and/or a hexagon. For connection points arranged in a connection point pattern, centre, bottom, side and/or top points of the connection points may be arranged in the connection point pattern.

The connection points may each have the same or different cross-sectional shapes, i.e. different shapes when seen orthogonally to the surface on which they are arranged, such as a circular, elliptical, and/or polygonal shape, such as a rectangular shape. A cross-sectional dimension and/or diameter of a cross-section of a connection point may be in the range of 50 µm-1 mm, such as 100 µm-750 µm, such as 200 µm-650 µm, such as 300-600 µm.

The distance and/or spacing between the connection points in a connection point pattern may be different between a connection point and each of the other connection points. Alternatively, or additionally, the distance between two or more of the connection points may be substantially the same or the same. The distance between the connection points, from a geometrical centre point of a connection point to a geometrical centre point of another connection point, may be in the range of 50 µm-1 mm, such as 100 µm-750 µm, such as 200 µm-650 µm, such as 300-600 µm.

In some embodiments, the first surface connection points have a substantially circular or circular cross-section. The first surface connection points may have a diameter in the range from 150 µm-300 µm, such as 230 µm. The second surface connection points may have a rectangular or substantially rectangular cross-section having a first side length in the range from 100 µm-300 µm, and a second side length in the range from 150 µm-450 µm.

The connection between respective connection points may be an electrical connection. An electrical connection may comprise electrical communication, e.g. by means of varying voltages, electric potentials and/or currents being applied to and/or running through, respectively, the one or more connection points. Alternatively, or in combination therewith, the electrical connection may comprise supplying a supply voltage, such as a V+ and V− connection, to the camera module.

The FPC may be in electrical communication with additional electrical/electronic components or elements and may at least partly redirect or forward communication to/from the additional electrical/electronic components or elements from/to the camera module through the converter circuit board.

The camera module may have a housing, in which image sensor and lens stack may be arranged. Outer surfaces of the camera module or a camera module housing of the camera module may be substantially box-shaped and/or parallelepipedal. The camera housing may house at least a part of the lens stack and/or a part of the image sensor.

The lens stack may be positioned distally of or in front of the image sensor, may include two or more lenses and may include a proximal lens and a distal lens. The camera module may further comprise a lens barrel which may hold and encase the lens stack. The lens stack may be stacked and/or the lens barrel may extend in a longitudinal direction. The connection surface may be positioned proximally of or behind the image sensor. The connection surface may face in a proximal direction. The lens stack or the lens barrel may have a longitudinally extending centre line, which may be, or may be coinciding with, a centre line of the camera module.

The at least one lens, potentially the plurality of lenses, may be of one or more types chosen from the group consisting of: concave, convex, plano-concave, plano-convex, bi-convex, bi-concave.

The tip part assembly may further comprise a working channel. The working channel may be substantially tubular and/or have a circumferentially extending, potentially substantially cylindrical or circular cylindrical, outer wall enclosing a working channel spacing. The working channel may have an inner diameter of 0.8 to 2 mm or 1 to 1.6 mm or 1 to 1.4 mm. A wall thickness of a circumferential wall of the working channel may be 0.1 to 0.5 mm.

The working channel may comprise a chamfered portion, which may face at least a part of the camera assembly. The chamfered portion may, additionally or alternatively, be provided as a canted-off portion, a bevelled portion, or the like. The chamfered portion may be abutting at least part of the camera assembly or may be positioned with a distance to the camera assembly.

The chamfered portion may be part of a circumferential wall of the working channel, where a such is provided, or may be formed in one piece with the wall. The wall thickness of the chamfered portion of the circumferential wall may thus be smaller than along at least one other portion of the circumferential wall.

The working channel may allow liquid to be removed from a body cavity and/or allow insertion of surgical instruments or the like into the body cavity. The working channel may be provided as a channel extending from a proximal end of an endoscope to a distal end of the endoscope to guide a tool and/or to provide suction. A connector and/or a connecting portion may be provided at the proximal end of the endoscope to allow insertion of a tool into the working channel and/or to allow suction to be applied to the working channel. In some embodiments, the working channel comprises a built-in or integrated tool at or in the tip part assembly. Such a tool may be suitable for grabbing, taking, and/or holding elements in a part of a patient, in which the endoscope tip part assembly is arranged during use.

In some embodiments, the working channel may similarly have a longitudinally extending centre line, which may extend from a proximal end to a distal end of the working channel. The centre line of the working channel may furthermore be parallel to a centre line of the of the camera module and/or a centre line of the insertion tube.

The camera module and a working channel may be positioned side-by-side or bottom-to-top. A top surface of the camera module may be positioned adjacent to and may be abutting or in contact with an inner top surface of the circumferential wall of a housing of the tip part assembly. See further below regarding such a housing. A bottom surface of the working channel may be positioned adjacent to and may be abutting or in contact with an inner bottom surface of the circumferential wall of the housing. The fold of the FPC may be directed towards an inner surface of the circumferential wall or may be directed towards a working channel. The fold of the FPC may be positioned adjacent to and may be abutting or in contact with an inner surface of the circumferential wall of the housing or with a portion of the working channel. A folding radius of the first fold may be in the range of 0.2-0.6 mm. In some embodiments, the folding radius may be in the range of 0.3-0.5 mm.

The camera assembly may comprise a mounting frame. The mounting frame may support and/or secure one or more in the group consisting of: the printed circuit board, one or more light sources, such as light emitting diodes (LEDs) potentially provided at the distal end of the tip part assembly, the lens barrel, and the image sensor.

An exterior flexible sleeve may be provided to extend around at least part of the tip part assembly, potentially of a housing thereof and/or around at least part of an insertion tube of the endoscope A maximum extent in the longitudinal direction from the distal end of the tip part assembly to a proximal end of the housing or FPC is in some embodiments 12, 10, or 8 mm.

The first connection point pattern and the second connection point pattern may be different in one or more of the entries of the group consisting of: a total number of the contact points, a size of one or more of the contact points, a shape of one or more of the contact points, and a relative position between the contact points.

A connection surface of the camera module may be a proximal end surface of the camera module.

The camera module may comprise a distal end surface and a proximal end surface opposite the distal end surface and facing a proximal end of the endoscope. The distal end surface may be abutting a housing of the tip part assembly or may be facing an exterior of the tip part assembly. The lens stack may be arranged such that this constitutes and/or abuts the distal end surface, so as to face the exterior, thereby allowing the camera module to obtain visual views of the exterior. The proximal end surface may be enclosed in a spacing of a housing circumferential wall.

The camera module may comprise a bottom surface which may be facing and/or may be abutting the working channel, and a top surface opposite the bottom surface. The top surface may be facing and/or abutting a circumferential wall of a housing.

The flexible printed circuit may comprise a first portion having a surface comprising the one or more FPC connection points arranged substantially in the second connection point pattern or in the second connection point pattern so that positions of the connection points of the second surface of the converter circuit board correspond to the flexible printed circuit surface connection points.

The FPC connection points may correspond substantially or correspond in size, shape, and/or relative position to the second surface connection points of the converter circuit board. For instance, the FPC connection points may have the same sizes, shapes, and/or relative position as the second surface connection points.

The first portion surface may be arranged face-to-face with the second surface connection points.

The FPC connection points may be connected to the corresponding converter circuit board connection points. In some embodiments, each of the FPC connection points are connected to a respective one of the converter circuit board connection points. The connection may be provided by ACF bonding.

The second connection point pattern may extend shorter than the first connection point pattern in a height direction of the connection surface.

This may be achieved e.g. by including a fewer number of rows of connection points in the second pattern, e.g. one single row, than the number of rows in the first pattern, e.g. two rows.

The height direction may extend from a bottom surface towards a top surface of the camera module. The top surface of the camera module may be positioned adjacent to or abutting a circumferential wall of a housing of the tip part assembly, see also further below.

The fold may be arranged within a projected cross-sectional area of the camera module along a longitudinal centre axis extending through a lens stack, image sensor, and connection surface of the camera module. This area may be positioned behind or proximally from the camera module towards a proximal end of the tip part assembly or of a housing of the tip part assembly.

Additionally or alternatively, the second connection pattern extends farther than the first connection point pattern in a width direction of the connection point surface.

The second connection point pattern may be positioned lower than the first connection point pattern in a height direction of the connection surface.

An entirety of the second pattern may be positioned below the first pattern.

A first connection point pattern may comprise four connection points arranged so that each connection point is positioned in a respective corner of a substantially rectangular shape. The second connection pattern may comprise four connection points disposed on the second surface along a substantially straight line.

The straight line may be positioned lower than a first and a second uppermost of the connection points or than a third and a fourth bottommost or lowermost of the connection points in a height direction of the connection surface.

Where the camera module and the first surface each comprise four connection points, the first connection point pattern may be rectangular, and a geometric centre point of each of the four connection points may form a respective corner in the rectangular connection point pattern. Alternatively, or additionally, top points, bottom points, or borders of each of the connection points may form a connection point pattern. A first and a second side of the rectangle, respectively, may be defined between the geometric centres of a connection point and two other connection points, such that an angle between the first and second sides of the rectangle is right or substantially right. The first side may have a length, i.e. a distance between the geometric centres of the two connection points defining this side, in the range of 350 µm-450 µm, such as 400 µm. The second side may have a length, i.e. a distance between the geometric centres of the two connection points defining this side, in the range of 400 µm-550 µm, such as 470 µm.

The flexible printed circuit connection points may be positioned on a first portion of the flexible printed circuit, the first portion being positioned face-to-face with the converter circuit board second surface. The first portion may extend into a second portion of the flexible printed circuit. The second portion may comprise a first fold towards the proximal end of the housing.

The fold may be at least partly positioned behind the camera module or the connection surface of the camera module towards a proximal end of the tip part assembly or of a housing thereof.

If the tip part assembly includes a working channel, the camera module may be positioned above the working channel within the housing so that a top surface of the camera module is positioned adjacent to the wall and a bottom surface of the camera module is positioned adjacent to the working channel. In that case, the second portion may extend upwardly from the first portion, the fold folding towards a proximal end of the tip part assembly or of a housing thereof. The camera module may be positioned above the working channel in the height direction.

The tip part assembly may further comprise a main circuit board connected to the flexible printed circuit second portion, the main circuit board extending in a direction away from the connection surface of the camera module.

The main circuit board may be included in the flexible printed circuit as a flexible printed circuit second portion. Alternatively, the main circuit board may be provided separately from and connected to a flexible printed circuit second portion, in which case it may be a rigid, printed circuit board (PCB).

Electrical components may be arranged on portions of the main circuit board. Electrical components may be passive components, such as capacitors, resistors or inductions, semiconductors, such as diodes or transistors, or wires, such as single wires, wire bundles, or FFCs, or any combination thereof.

The tip part assembly may further comprise a housing having a circumferentially extending outer surface for facing the environment. The outer surface may enclose a volume and may extend in a longitudinal direction between a proximal end and a distal end of the housing. The working channel may be at least partly housed in the housing and may comprise an opening in a distal surface of the housing. The camera module may be at least partly housed in the housing. At least a portion of the flexible printed circuit and at least a portion of the converter circuit board may be arranged in the housing.

The camera module and/or the FPC may be at least partly or fully shielded electrically and/or from liquid from the body of a patient when the endoscope is in use. This may, in turn, mitigate a risk of failure due to electrical short-circuiting as well as a risk of electrically shocking a patient on which the endoscope is used.

Furthermore, an advantage of the tip part assemblies according to this disclosure may be that the need for material of the housing to provide electrical insulation may be reduced by the arrangement of the FPC. By the fold of the FPC being arranged behind the camera module, the FPC may be positioned further from the housing wall than if arranged in the top volume, thereby using the dielectric properties of the air or of a material arranged between the FPC and the housing wall, such as a potting material where such is provided in the housing.

The housing may comprise an end wall arranged at a distal end of the housing and/or forming the distal end of the housing. The end wall may be formed in one piece with other parts of the housing. The end wall may comprise an opening to the exterior of the housing for a working channel and/or may comprise a window towards the exterior of the housing for the camera module.

In some embodiments a potting material, such as an adhesive, may be provided in the housing. The potting material may fill out any or parts of a spacing between the components, e.g. the working channel, the camera module, and/or the FPC, or the sections thereof arranged inside the housing.

The housing may be tubular and/or cylindrical or substantially cylindrical and/or circular cylindrical or substantially circular cylindrical. The working channel or a part thereof may be in one piece with the housing and/or may be provided as a separate part. The working channel may comprise a first portion potentially provided in one piece with the housing, and a second portion interconnected with the first portion. The working channel second portion may be provided as a flexible tube and may be interconnected to the first portion by means of an adhesive.

The housing may provide electrical insulation and/or water tightness around the FPC and electrical connections within the housing and may form a mold or container for adhesive and/or potting material poured or injected into the housing. The housing may ensure that a minimum insulation thickness is present on one or more sides or all outer surfaces of the tip part assembly. If an adhesive or a potting material is present in the housing, this may provide greater robustness, mechanical stability and/or rigidity of the tip part assembly, and/or better attachment/fixation of components within the housing. This may be advantageous since wires or cables may be pulled during operation of the endoscope, pulling also in the FPC, especially during bending of a bending section of the tip part assembly.

Molding of the housing may occur as a two-component molding in which two different materials are molded in the same mold. For example, an end wall arranged at and/or forming a distal end of the housing may be molded in a first material, which may be transparent, and the circumferential wall may be molded in a second, different material, which may be non-transparent and may include higher adhesive compatibility with an adhesive or potting material in the housing. Alternatively, the circumferential wall can be manufactured separately from the end wall. For example, the two walls can be molded separately, or the end wall can be molded, and the circumferential wall extruded. In this case, the circumferential wall and the end wall can be adhered to each other by means of an adhesive.

The housing may comprise a tubular wall enclosing a volume, the volume being a spacing within the housing. This spacing may also be defined by a distal end wall of the housing. An opening for the working channel may be provided in the end wall. The camera module and potentially other components of the tip part assembly may be at least partly housed within the spacing and potentially attached, potentially by means of adhesive, to the housing. The housing may be a molded part, and the spacing may be at least partly filled with a hardened adhesive, the hardened adhesive being provided separately from the housing. Alternatively, the housing may take the form of a hardened adhesive in which the camera module and potentially other components may be embedded.

A lateral portion of the volume of the housing may be defined laterally from the camera module and the working channel, the lateral volume extending between the proximal end and the distal end of the housing. An FPC first portion or connections thereof may be electrically connected to the at least one connection of the connection surface.

The housing may be an outer or exterior housing which may be exterior with respect to elements housed or enclosed therein, such as the camera module, the FPC, wires, electrical components, LEDs, and the like.

An outer maximum extent in a cross sectional direction of the tip part assembly may be less than 3.3 mm.

The cross sectional direction may extend at a right angle to the above-mentioned longitudinal direction.

This outer maximum extent may be a maximum outer diameter of the tip part assembly and may be a maximum cross sectional extent or a maximum diameter of a housing of the tip part assembly. The outer maximum extent may be less than 3.2, 3.1, 3.0, 2.9, 2.8, 2.7, 2.6 or 2.5 mm.

The converter circuit board may further comprise at least one LED holder for holding and/or supporting a light emitting diode, LED.

The LED holder may be configured for attachment of and holding an LED. The LED may be attached to the LED holder, potentially to shine towards a distal end of the tip part assembly or of a housing of the tip part assembly.

A first portion of the converter circuit board may be positioned face-to-face with the connection surface of the camera module. A second portion of the converter circuit board may comprise the LED holder. This second portion may extend from and away from this first portion in a lateral direction and potentially beyond the connection surface of the camera module. This lateral direction may extend transverse to the height direction mentioned above.

A third portion of the converter circuit board may extend from and away from the first portion of the converter circuit board in a lateral direction substantially opposite to the lateral direction in which the second portion of the converter circuit board extends and potentially beyond the connection surface of the camera module. The converter circuit board third portion may comprise an LED holder. This opposite lateral direction may similarly extend transverse to the height direction.

The LED holder may lead to and establish an electrical connection with respective LED(s) of the tip part assembly. The LED(s) may be positioned within a volume or spacing of the tip part assembly, or a housing thereof. The LED holder portions may extend away from the connection points of the converter circuit board.

The LED holder may be electrically connected to the at least one LED by soldering and/or by anisotropic conductive adhesives (ACA), such as anisotropic conductive film (ACF) or anisotropic conductive paste (APC) bonding.

The LEDs may be arranged at the distal end of the tip part assembly or abutting one or more light guides (see description below) arranged at the distal end of the tip part assembly, and may have a connection surface extending substantially in parallel or in parallel to the connection surface of the camera module. The one or more LED holders may extend in parallel or substantially in parallel to the connection surface of the at least one LED. The LEDs may be arranged beside the camera module.

The LEDs may comprise a light emitting surface. The light emitting surface(s) may emit light in the proximal-distal direction. The light emitting surface(s) may be positioned in abutment with a housing, where this is provided, or in abutment with one or more light guides.

The tip part assembly may also include one or more light guides for guiding light from respective LED(s) to e.g. a front or distal end surface or end wall of the tip part assembly and/or a housing thereof. One or more light guides may be in one piece, potentially molded in one piece with, a housing of the tip part assembly. The light guide(s) may extend from the distal end of the tip part assembly to a respective LED or a respective set of LEDs. In some embodiments, the light guides are made from a transparent material. The light guide(s) may be molded and/or may comprise a portion abutting the camera module and/or be arranged in front of the lens stack.

The tip part assembly may further comprise a bending section which may have a distal end segment which may be connected to a housing of the tip part assembly.

This may allow for the tip part assembly to be manoeuvred inside the body cavity. Thereby, various places inside the body cavity may be inspected by means of the camera assembly, and/or the working tool or suction may, by means of the working channel, be applied at various places inside the body cavity.

The bending section may comprise a number of hingedly interconnected segments including a distal end segment, a proximal end segment, and a plurality of intermediate segments positioned between the proximal end segment and the distal end segment. At least one hinge member may interconnect adjacent segments with each other. The bending section may be a section allowing the tip part assembly to bend relative to an insertion tube, potentially so as to allow an operator to manipulate the tip part assembly while inserted into a body cavity of a patient. The bending section may be molded in one piece or may be constituted by a plurality of molded pieces.

In some embodiments, the housing may be connected to the distal end segment of the bending section. The housing may be connected to the distal end segment at a proximal end of the housing. The working channel may extend into and/or through the distal end segment and/or the bending section.

A second aspect of this disclosure relates to a method for assembly of a tip part assembly for an endoscope, the method comprising the steps of a) providing a flexible printed circuit of the tip part assembly, the flexible printed circuit having two or more connection points, b) providing a camera module of the tip part assembly, the camera module comprising a connection surface comprising two or more connection points for electrical communication of the camera module with the connection points of the flexible printed circuit, the connection points of the connection surface being arranged in a first connection point pattern, and c) providing a converter circuit board of the tip part assembly, the converter circuit board comprising a first surface and a second surface opposite the first surface, the first surface of the converter circuit board comprising connection points similarly arranged substantially in the first connection point pattern so that positions of the first surface connection points correspond to the connection surface connection points, the second surface of the converter circuit board comprising connection points arranged in a second connection point pattern, the second connection point pattern being different from the first connection point pattern, d) connecting the first surface connection points to the connection surface connection points so that positions of the first surface connection points correspond to associated positions of the connection surface connection points, and e) connecting the second surface connection points to the connection points of the flexible printed circuit.

The steps of the method according to this second aspect may be performed in any order, not necessarily in sequence. The steps may be carried out in the sequence a), b), c), d), e), or may alternatively be carried out in the sequence a), b), c), e), d). The steps a), b), and c) may be carried out in any sequence or may alternatively be carried out simultaneously.

The first surface connection points may be arranged in the first connection point pattern.

The method may provide identical or similar advantages to the tip part assembly according to the first aspect of this disclosure. Embodiments of the tip part assembly of this method may be the same as described with respect to the tip part assembly according to the first aspect of the disclosure.

The method may comprise the further steps of: f) providing a housing having a circumferentially extending, substantially cylindrical and tubular wall, enclosing a spacing and extending in a longitudinal direction, and g) subsequent to steps d) and e) arranging at least a part of the camera module, at least a part of the flexible printed circuit, and at least a part of the converter circuit board in the spacing.

The housing may be a housing according to any one of the above embodiments of this.

The tip part assembly assembled by means of the method may be according to the first aspect of this disclosure.

A third aspect of this disclosure relates to a tip part assembly for an endoscope, the tip part assembly being manufactured according to the second aspect of this disclosure.

This tip part assembly may provide identical or similar advantages to the tip part assembly according to the first aspect of this disclosure. Embodiments of the tip part assembly of this method may be the same as described with respect to the tip part assembly according to the first aspect of the disclosure.

A fourth aspect of the present disclosure relates to an endoscope comprising a tip part assembly according to the first aspect of this disclosure or a tip part assembly according to this third aspect of the disclosure.

The endoscope may comprise a control element. The control element may be configured to allow an operator to control a tip part assembly of the insertion tube by at least one steering wire. The control element may allow bending the tip part assembly in at least one direction, potentially in two directions, the two directions potentially being opposite. The control element may be accommodated in an operating handle. The control element may include a lever allowing an operator to control the control element. The lever may extend outwardly from the control element, potentially through an operating handle. The control element may be in the form of a roller or a roller disc.

The endoscope may comprise an operating handle. The operating handle may be suitable for allowing an operator to grip and to operate the endoscope, potentially with one hand.

The operating handle may comprise a handle housing arranged at a proximal end of the insertion tube. The handle housing may accommodate the control element.

The insertion tube and/or a distal end thereof and/or the tip part assembly thereof may be suitable for insertion into a body cavity, potentially a kidney, through a body opening, potentially a urinary passage or a urethra. The body may be a natural and/or artificial body, potentially a human body. The insertion tube may extend from the operating handle towards a distal end of the endoscope.

Additionally or alternatively, the endoscope may form part of a system for visually inspecting inaccessible places such as human body cavities, the system further comprising a monitor. The endoscope may be connectable to the monitor, and the monitor may allow an operator to view an image captured by the camera assembly of the endoscope.

A person skilled in the art will appreciate that any one or more of the above aspects of this disclosure and embodiments thereof may be combined with any one or more of the other aspects of the disclosure and embodiments thereof.

BRIEF DESCRIPTION OF DRAWINGS

The tip part assembly assemblies and methods will now be described in greater detail based on non-limiting exemplary embodiments and with reference to the drawings, on which:

FIG. 4a shows a distal end view of a first embodiment of a tip part assembly of FIGS. 1a and 1b, FIG. 4b shows a cross-sectional view of the tip part assembly of FIGS. 1a and 1b, FIG. 4c shows a second cross-sectional view of the tip part assembly of FIGS. 1a and 1b, taken orthogonally to the cross-sectional view of FIG. 4b along the line A-A of FIG. 4a, FIG. 5a shows a perspective view of the tip part assembly of FIGS. 1a and 1b.

Similar reference numerals are used for similar elements across the various embodiments and figures described herein.

DETAILED DESCRIPTION

Figure 1A:
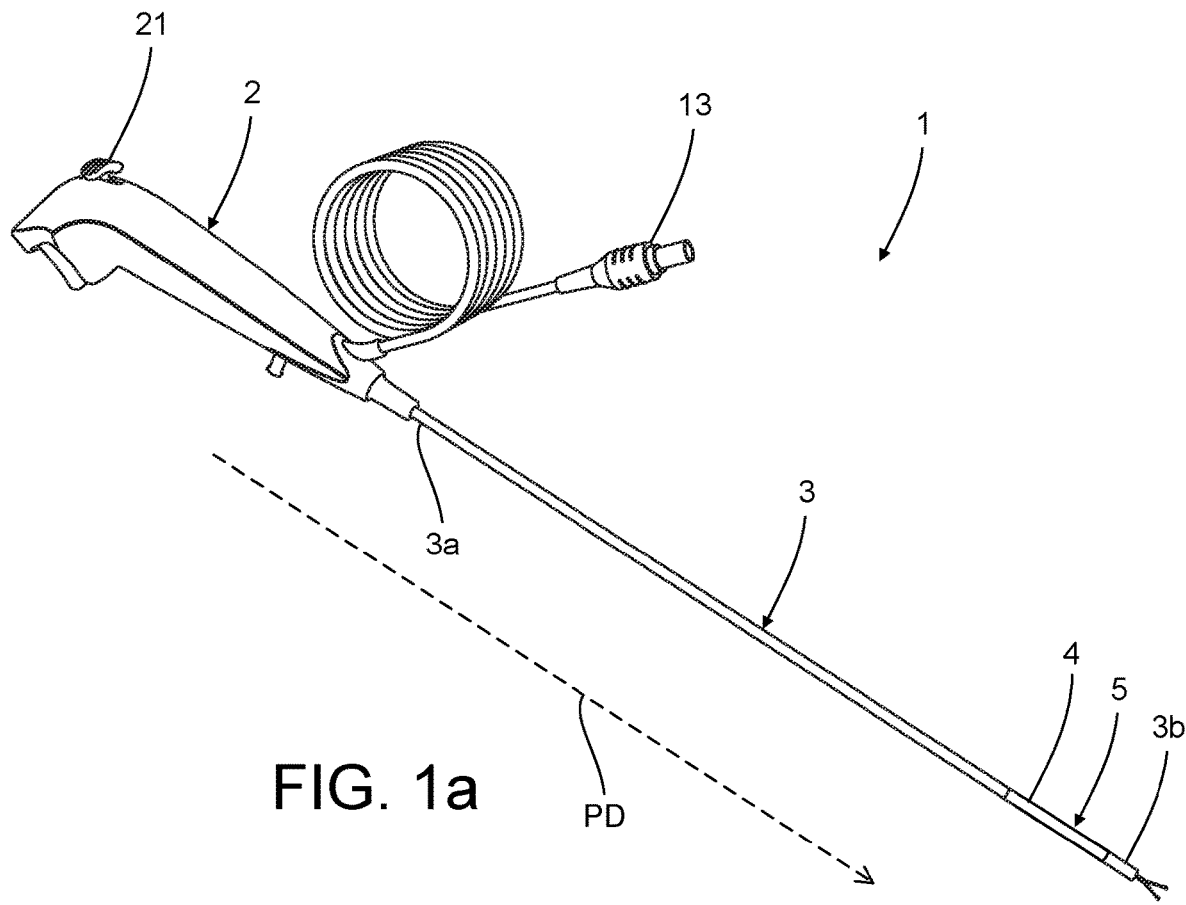
FIG. 1a shows a perspective view of an endoscope in which a tip part assembly according to the present disclosure is implemented.

Referring first to FIG. 1a, an endoscope 1 is shown. The endoscope is disposable, and not intended to be cleaned and reused. The endoscope 1 comprises an elongated insertion tube 3. At the proximal end 3a of the insertion tube 3 an operating handle 2 is arranged. The operating handle 2 has a control lever 21 for manoeuvring a tip part assembly 5 at the distal end 3b of the insertion tube 3 by means of a steering wire. A camera assembly 6 is positioned in the tip part assembly 5 and is configured to transmit an image signal through a monitor cable 13 of the endoscope 1 to a monitor 11.

Figure 1B:
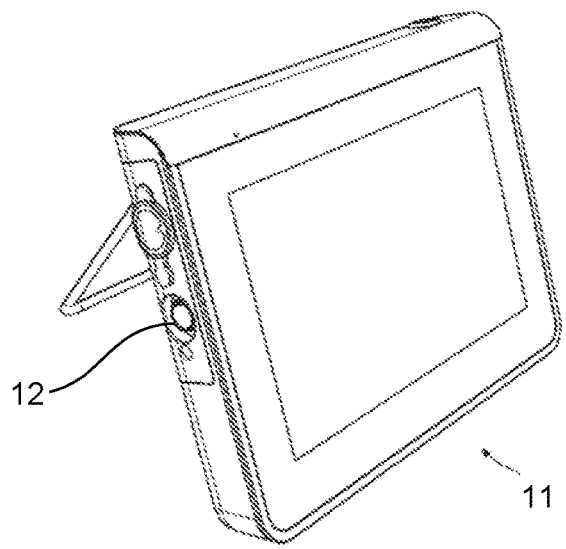
FIG. 1b shows a perspective view of a monitor to which the endoscope of FIG. 1a is connected.

In FIG. 1b, a monitor 11 is shown. The monitor 11 may allow an operator to view an image captured by the camera assembly 6 of the endoscope 1. The monitor 11 comprises a cable socket 12 to which a monitor cable 13 of the endoscope 1 can be connected to establish a signal communication between the camera assembly 6 of the endoscope 1 and the monitor 11.

The proximal-distal direction PD is an axis extending along the parts of the insertion tube 3 of the endoscope 1.

Figure 2A:
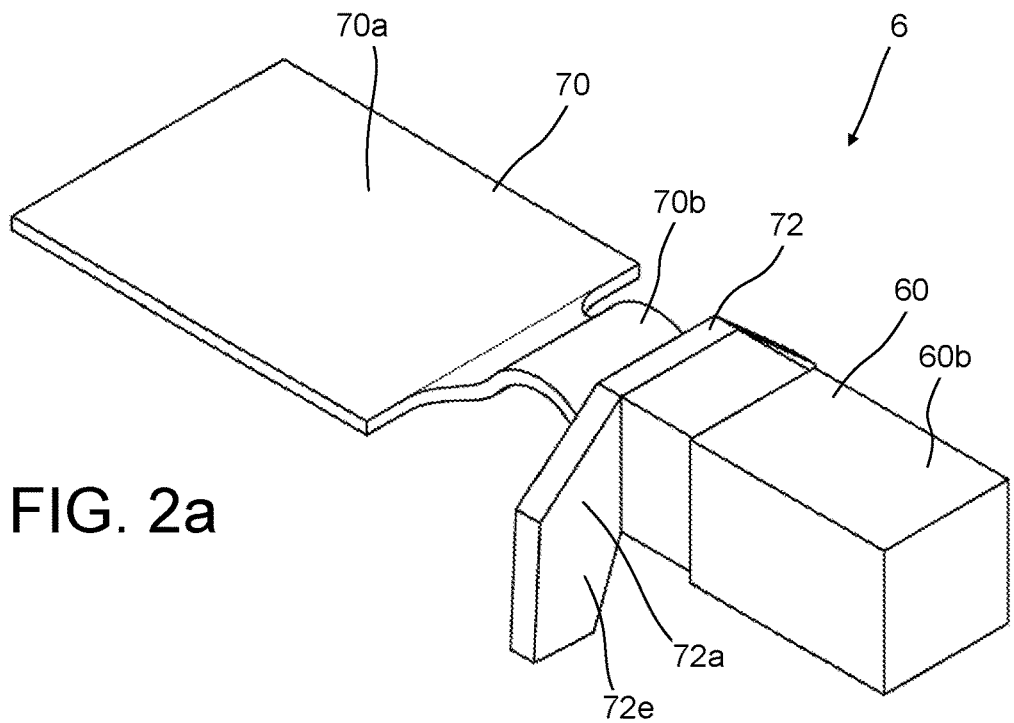
FIG. 2a shows a perspective view of a first camera assembly of the tip part assembly of FIGS. 1a and 1b.
Figure 2B:
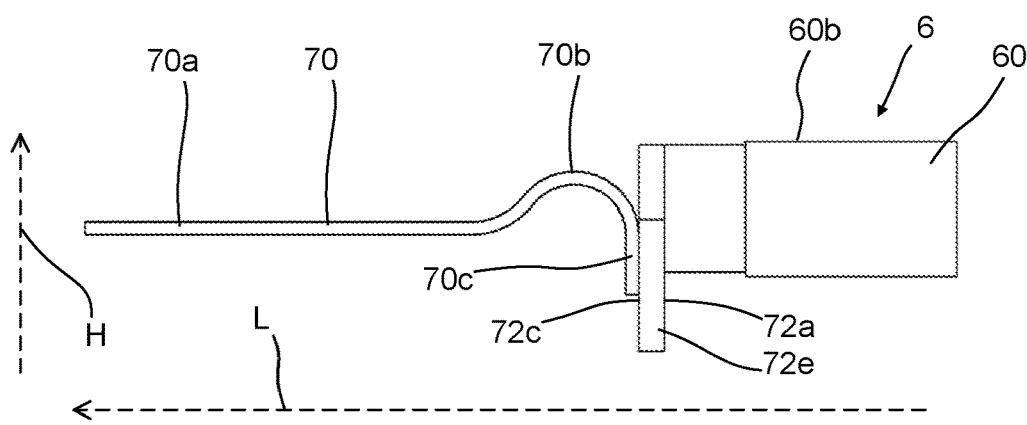
FIG. 2b shows a side view of the first camera assembly of the tip part assembly of FIGS. 1a and 1b.

Referring to FIGS. 2a and 2b, a camera assembly 6 is shown. FIGS. 3a-3d show a camera module 60, a converter circuit board 72, and a flexible printed circuit (FPC) 70 of the camera assembly 6 of FIGS. 2a and 2b. FIGS. 4a-4c and 5a show a tip part assembly comprising the camera assembly 6 of FIGS. 2a and 2b.

The tip part assembly 5 comprises the flexible printed circuit 70 having four connection points 70d and a camera assembly 6 comprising a camera module 60 having a connection surface 60a comprising four connection points 60c for electrical communication of the camera module with the connection points 70d of the flexible printed circuit 70. The connection points 60c of the connection surface 60c are arranged in a first connection point pattern. The camera assembly 6 further comprises a converter circuit board 72 comprising a first surface 72a and a second surface 72c opposite the first surface 72a. The first surface 72a of the converter circuit board 72 comprises connection points 72b similarly arranged in the first connection point pattern so that positions of the first surface connection points 72b correspond to the connection surface connection points 60c. The second surface 72c of the converter circuit board 72 comprises connection points 72d arranged in a second connection point pattern. The second connection point pattern is different from the first connection point pattern.

The first surface connection points 72b are connected to the connection surface connection points 60c so that positions of the first surface connection points 72b correspond to associated positions of the connection surface connection points 60c. The second surface connection points 72d are connected to the connection points 70d of the flexible printed circuit 70. The FPC connection points 70d are arranged on a surface of a first portion 70c of the FPC 70.

So, instead of folding the FPC 70 such that substantially an entire fold 70b of the FPC 70 is located in a top volume 8d of a housing 8 as in the prior art, which means that the top volume 8d of the housing 8 above a top level of the camera module 60 must provide room for the FPC fold 70b, the FPC 70 is here folded such that the substantially entire fold 70b or the entire fold 70b is arranged in a volume behind the camera module 60, i.e. proximally of the camera module 60, when seen in a proximal-distal direction PD of the endoscope 1.

This means that the extent of the housing 8 in a height direction H can be reduced compared to the prior art. This is due to the height direction H typically being decisive for the necessary diameter or cross-sectional extent of the housing 8 since there is more room at a lateral side of the camera module 60. Two lateral sides are located adjacent to the camera module 60 in the lateral direction T and in a direction opposite the lateral direction T, respectively.

An outer diameter of the housing 8 is 3.0 mm.

The proximal-distal direction PD is defined as a direction extending along the parts of the insertion tube 3 of the endoscope 1. The proximal-distal direction PD is a centre line of the insertion tube 3.

The distal end of the tip part assembly forms a distal end of the endoscope 1.

Figure 6:
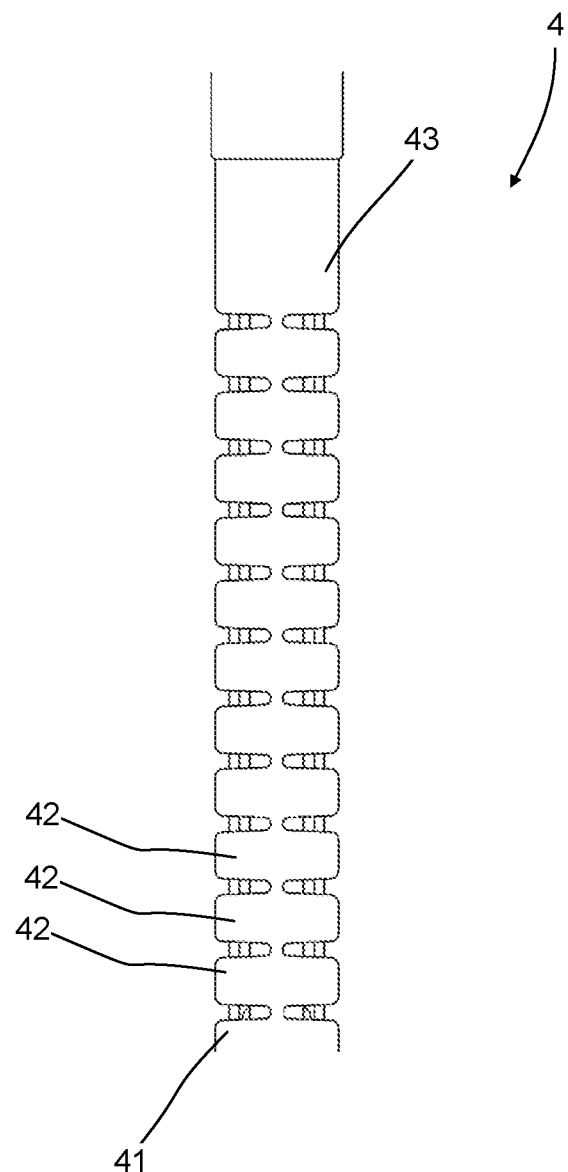
FIG. 6 shows a side view of a bending section of the endoscope of FIG. 1a and FIG. 1b, and FIGS. 7a and 7b show distal, or camera side, and proximal, or bending section side, views of the converter circuit board of the tip part assembly of FIGS. 1a and 1b.

The tip part assembly has a proximal end for being connected to other parts of the endoscope 1, i.e. to a distal end segment 41 of a bending section 4, as e.g. shown on FIG. 6, and a distal end positioned oppositely from the proximal end for forming a distal end of the endoscope 1. A longitudinal direction L extends from the proximal end towards the distal end of the tip part assembly. A height direction H extends transversely to the longitudinal direction. A lateral direction T extends transversely to the longitudinal L and height directions H. Angles between these three directions are right.

The FPC 70 is a single-sided flexible circuit or a rigid-flex circuit and comprises one layer of conductive material and two layers of insulating material.

A main circuit board is provided as a second portion 70a of the FPC 70 and is electrically connected to other parts (not shown) of the endoscope by wires (not shown) being soldered onto the FPC second portion 70a.

The converter circuit board 72 is a rigid printed circuit board (PCB) comprising two, layers of copper and one layer of insulating materials, such as FR-4, in between the two layers of copper. A solder mask layer is applied to each of the two copper layers.

The converter circuit board 72 extends in a plane and is larger than the connection surface 60a of the camera module 60. The converter circuit board 72 has a substantially identical extent in a height direction as the connection surface 60a and has a longer extent in the lateral direction L than the connection surface 60a.

The connection points 72b, 72d are provided as solder pads which have an electrically conducting material, i.e. solder paste, on a surface thereof. The connection points 70d, 72b, 72d of the converter circuit board 72 and/or of the FPC 70 are provided as solder pads for soldering and/or ACF bonding to a respective other connection point.

Figure 3A:
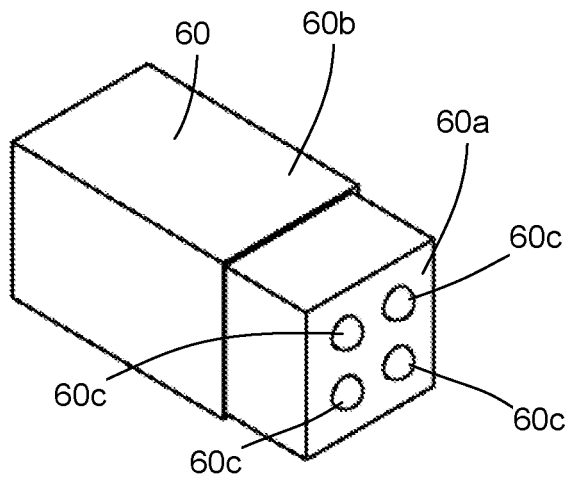
FIG. 3a shows a perspective view of a camera module of the first camera assembly of a tip part assembly of FIGS. 1a and 1b.
Figure 3B:
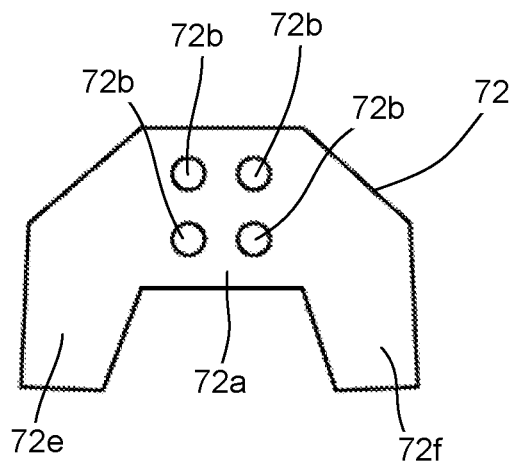
FIG. 3b shows a distal end view of a converter circuit board of the first camera assembly of the tip part assembly of FIGS. 1a and 1b.
Figure 3C:
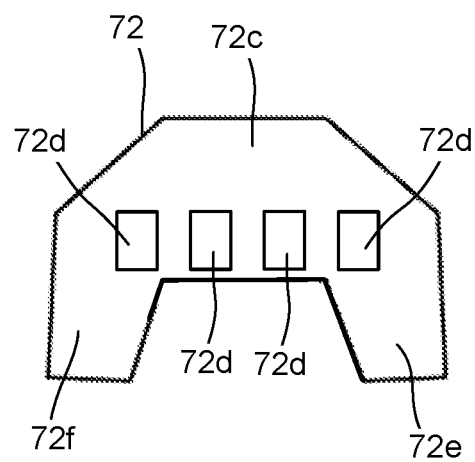
FIG. 3c shows a proximal end view of the converter circuit board of the first camera assembly of the tip part assembly of FIGS. 1a and 1b.
Figure 3D:
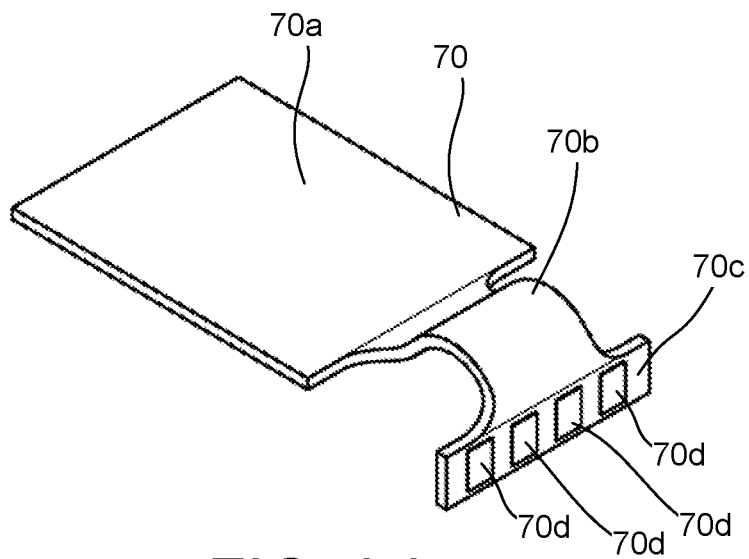
FIG. 3d shows a perspective view of a flexible printed circuit of the first camera assembly of the tip part assembly of FIGS. 1a and 1b.
Figure 7A:
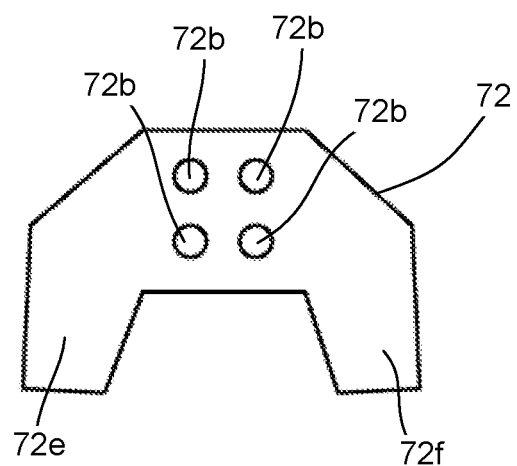
Figure 7B:
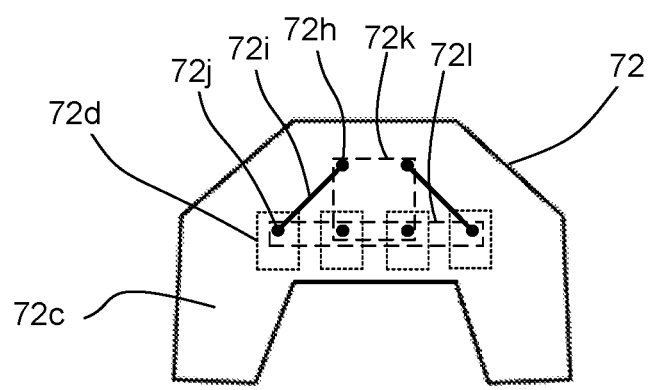

Each of the second surface connection points 72d are in electrical connection with a respective one of the first surface connection points 72b. The electrical connection is a low resistance connection and is provided by internal routing in the converter circuit board 72. Referring to FIGS. 7a and 7b, the distal, or first, surface of the converter circuit board is on the camera module side, and the proximal, or second, surface is on the proximal side, or FCB side, of the converter circuit board. FIG. 7a is a reproduction of FIG. 3b showing connection points 72b in the first connection point pattern, also referred to as the camera module connection pattern 72k (shown in FIG. 7b), so that positions of the first surface connection points 72b correspond to the connection surface connection points 60c. In other words, the positions of the connection points 72b match the positions of the connection points of the camera module.

An embodiment of a method of making the converter circuit board 72 will now be described with reference to FIGS. 7a and 7b. The converter circuit board 72 can be made by depositing or etching copper tracings on one and/or the other side of the converter circuit board 72 to connect solder pads on one side with solder pads on the opposite side. FIG. 7b shows the FCB side of the converter circuit board, and also shows the camera module connection pattern 72k and the second connection point pattern, or FCB connection pattern 72l. Four vias 72h are shown in the camera module connection pattern 72k, two upper and two lower vias. Two additional vias 72j align with the two lower vias 72h to form the FCB connection pattern 72l. Copper tracings 72i connect upper vias 72h with vias 72j. Solder pads are placed over the lower vias 72h and the vias 72j. The vias comprise holes that connect opposite sides of the converter circuit board 72. Solder or copper or any conductive material can be placed in the holes to connect solder pads and copper tracings on one side with solder pads and copper tracings on the opposite side of the converter circuit board 72.

In variations described below, the FCB connection pattern is located on the converter circuit board closer to a working channel than the camera module connection pattern. Thus, copper tracings extend also from the lower vias 72h. In this respect, the FCB connection pattern is located lower than the camera module connection pattern.

The first and second connection point patterns shown in FIGS. 7a and 7b are illustratively. Other patterns are also possible, and the patterns should be arranged such that none of the connection points in the second connection point pattern are closer to the upper surface of the camera module (e.g. closest to the inner surface of the housing) than a connection point in the first connection point pattern that is closest to the upper surface than other of the connection points in the first connection point pattern. Thus, the second connection point pattern could be the same as the first connection point pattern but offset along the height extent so that it is closer to the working channel than the first connection point pattern. In this manner, the fold of the flexible circuit does not extend above the projection of the camera module or the camera module projection volume and a smaller endoscope cross-section can be achieved.

The connection surface connection points 60c of the camera module 60 are provided as solder balls including a solder material and protruding from the connection surface 60a. The connection surface connection points 60c have a circular cross-section when seen in a direction perpendicular to the connection surface. The solder material is arranged in a substantially hemisphere shape or hemisphere shape on each connection surface connection point 60c. The connection points 60c form a ball grid array (BGA).

The first surface connection points 72b have a circular cross-section. The first surface connection points 72b each have a diameter of 230 μm. The second connection points 71d have a rectangular cross-section having a first side length in the range from 100 μm-300 μm, and a second side length in the range from 150 μm-450 μm.

The FPC 70 comprises a connection surface 70c comprising connection points 70d arranged in the second connection point pattern so that positions of the connection points 72d of the second surface 72c, 72c' of the converter circuit board 72, 72' correspond to the flexible printed circuit surface connection points 70d.

The FPC connection points 70d correspond in size, shape, and relative position to the second surface connection points 72d of the converter circuit board 72, 72'. The FPC connection points 70d have the same sizes, shapes, and/or relative position as the second surface connection points 72d.

The connection surface 70c of the FPC 70 comprising the connection points 70d is arranged face-to-face with the second surface connection points 72d.

Each of the FPC connection points 70d are connected to a respective one of the converter circuit board connection points 72d.

The second connection point pattern extends shorter than the first connection point pattern in the height direction H of the connection surface 70c.

This is achieved by including one row of connection points 70d, 72d in the second pattern as opposed to two rows of connection points 60c, 70b in the first pattern.

The height direction H extends from a bottom surface towards a top surface 60b of the camera module 60.

The camera assembly 6 is a sub-assembly of the tip part assembly 5 and comprises a camera module 60 with a housing, in which the image sensor (not shown) and lens stack (not shown) are arranged and housed, the converter circuit board 72, and the FPC 70. Outer surfaces of the camera module 60 are substantially box-shaped. The connection surface 60a is positioned proximally of the image sensor. The connection surface 60a faces in a proximal direction.

The tip part assembly further comprises a working channel 7. The working channel 7 is tubular and has a circumferentially extending, circular cylindrical, outer wall 7g enclosing a working channel spacing. The working channel has an inner diameter of 1.2 mm. A wall thickness of a circumferential wall of the working channel 7 is 0.3 mm.

The working channel 7 comprises a chamfered portion 7d, which may face at least a part of the camera assembly 6. The chamfered portion 7d is positioned with a distance to the camera assembly 6.

The chamfered portion 7d is a part of the circumferential wall of the working channel 7 and is formed in one piece with the wall.

The working channel 7 is provided as a channel extending from a proximal end of the endoscope 1 to a distal end of the endoscope 1 to guide a tool and/or to provide suction.

The camera module 60 and the working channel 7 are positioned bottom-to-top. The camera module 60 comprises a bottom surface facing the working channel 7, and a top surface 60b opposite the bottom surface. The top surface 60b of the camera module 60 is positioned adjacent to an inner top surface of a circumferential wall 8g of a housing 8 of the tip part assembly 5. The fold 70b of the FPC 70 is directed towards an inner top surface of the circumferential wall 8g.

Figure 2C:
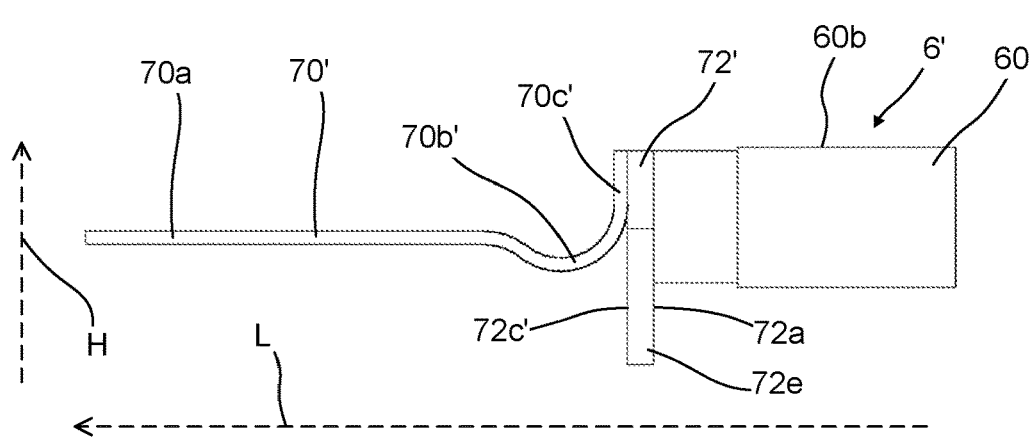
FIG. 2c shows a side view of a second, alternative camera assembly of an embodiment of a tip part assembly according to the present disclosure.

In the embodiment of the camera assembly 6' shown in FIG. 2c, comprising the camera module 60 similar to that of the first embodiment of the camera assembly 6, an FPC 70' has a second portion 70a, i.e. formed in one piece with a main circuit board, a fold 70b' and a first portion 70c'. The fold is directed towards a working channel 7, i.e. downwards in the height direction H. The camera assembly 6' further comprises a converter circuit board 72', having similar features to the converter circuit board 72 of the first camera assembly embodiment, except from the connection points (not shown) of the second portion 72c' thereof being moved upwards in the height direction H to connect with connection points (not shown) of the FPC first portion 70c'. The connection points and the second connection point pattern of the FPC first portion 70c' and of the second surface 72c' are similar to those of the FPC first portion 70c and the second surface 72c of the first embodiment of the camera assembly 7.

A folding radius of the first fold 70b, 70b' is 0.4 mm.

The tip part assembly comprises a housing 8, 8' having a circumferentially extending outer surface 8c for facing the environment. The outer surface 8c encloses a volume and extends in the longitudinal direction L between the proximal end 8a and distal end 8b of the housing 8, 8'. The working channel 7 is partly housed in the housing 8, 8' and comprises an opening 7c in a distal surface, i.e. the end wall 8e, 8e', of the housing 8, 8'. The camera module 60 is housed in the housing 8, 8'. The flexible printed circuit 70 and the converter circuit board 72 are arranged in the housing 8, 8'. A top volume 8d of the housing 8, 8' is defined above the camera module 60 in the height direction H and extending along the housing 8, 8' in the longitudinal direction L. A camera projection volume 8h of the housing 8, 8' is defined as the volume extending proximally of the camera module along the longitudinal direction L and having a cross-section equal to a maximum cross-section of the camera module orthogonal to the longitudinal direction.

The housing comprises an end wall 8e, 8e' forming the distal end 8b of the housing 8, 8'. The end wall 8e, 8e' comprises an opening to the exterior of the housing for a working channel. The end wall 8e further comprises a window 8f, i.e. an opening, towards the exterior of the housing 8, 8' for the camera module 60.

The housing 8, 8' is tubular and circular cylindrical. A first portion of the working channel 7a is formed in one piece with the housing 8, 8'. A second portion of the working channel 7b is provided as a separate part and interconnected with the first portion. The working channel second portion 7b is a flexible tube and is interconnected to the first portion 7a by means of an adhesive.

The housing end wall 8e, 8e' forming a distal end 8b of the housing 8, 8' is molded in a first, transparent material and the circumferential wall is molded in a second, different material, which is non-transparent and includes higher adhesive compatibility with an adhesive or potting material in the housing 8, 8'.

A maximum extent in the longitudinal direction L from the distal end 8b of the tip part assembly to the proximal end 8a of the housing is 10 mm.

A connection surface 60a of the camera module 60 is a proximal end surface of the camera module 60.

The camera module 60 comprises a distal end surface and a proximal end surface, i.e. the connection surface 60a, opposite the distal end surface and facing a proximal end of the endoscope. The distal end surface is facing an exterior of the tip part assembly 5. The lens stack is arranged such that this abuts the distal end surface, so as to face the exterior, thereby allowing the camera module 60 to obtain visual views of the exterior. The connection surface 60a is enclosed in a spacing of a housing circumferential wall 8g.

Figure 5A:
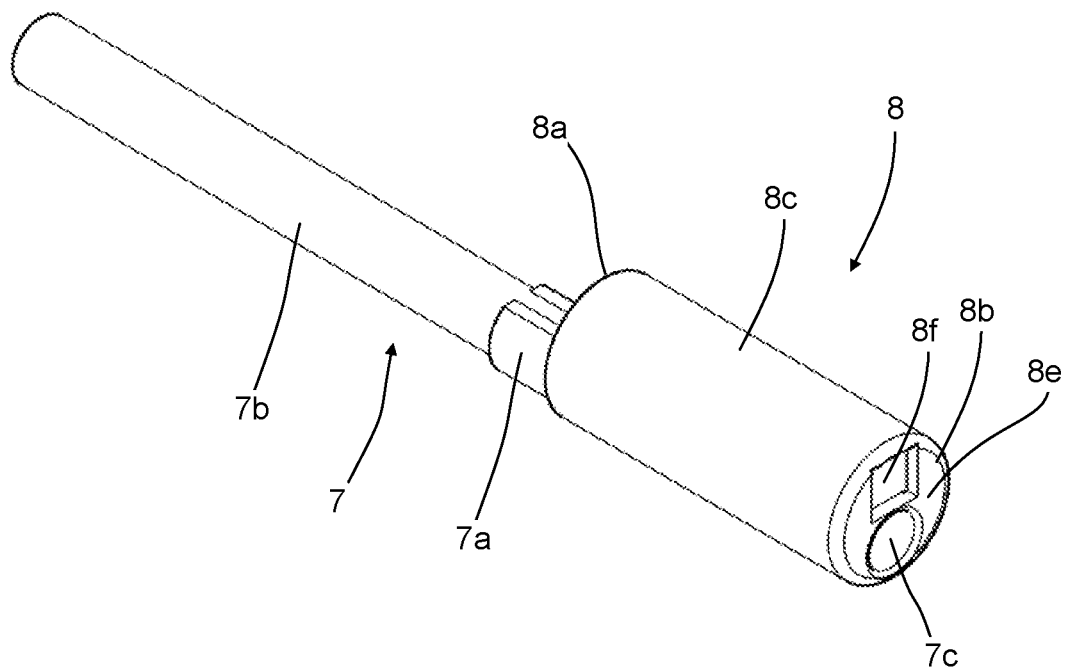
FIG. 5b shows a perspective view of a second, alternative embodiment of a tip part assembly according to the present disclosure.
Figure 5B:
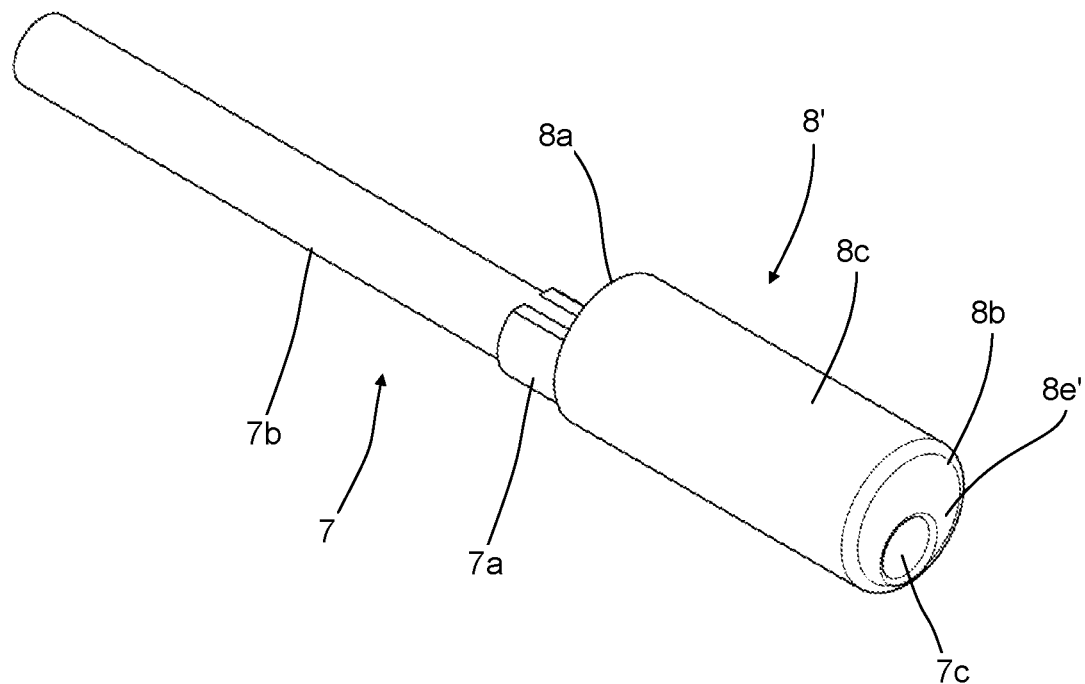

As seen in FIG. 5b, showing a distal tip part assembly with a working channel 7 similar to that of the first embodiment of the distal tip part assembly 5, and a housing 8' having a proximal end 8a, a distal end 8b and a circumferential wall similar to those of the housing 8, an end wall 8e' does not have a window for a camera module (not shown). The end wall 8e' is here made from a transparent material, and the camera module abuts the end wall 8e' of the housing 8', thereby allowing the camera module to obtain visual views of the exterior.

The fold 70b, 70b' is arranged within a projected cross-sectional area of the camera module along a longitudinal centre axis (not shown) extending through a lens stack, image sensor, and connection surface 60a of the camera module 60. The longitudinal centre axis extends parallel to the longitudinal direction. This area is positioned behind, i.e. proximally, from the camera module 60 towards a proximal end 8a of the housing 8, 8' of the tip part assembly 5.

The second connection pattern is a straight line extends farther than the first connection point pattern in a lateral direction L of the connection surface 70c, 70c'.

The second connection point pattern is positioned lower than the first connection point pattern in the height direction H of the connection surface 70c, 70c'.

An entirety of the second connection point pattern is positioned below the first pattern.

The first connection point pattern comprises four connection points 60c, 72b arranged so that each connection point 60c, 72b is positioned in a respective corner of a substantially rectangular shape. The second connection point pattern comprises four connection points 72d disposed on the second surface 72c along a straight line. A first and a second respective side of the rectangular shape of the first connection point pattern is defined between the geometric centers of a connection point 60c, 72b and two other connection points 60c, 72b, such that an angle between the first and second sides of the rectangle is right. The first side has a length, i.e. a distance between the geometric centers of the two connection points 60c, 72b defining this side, of 400 μm. The second side has a length, i.e. a distance between the geometric centers of the two connection points 60c, 72b defining this side, in the range of 470 μm.

The straight line of the second connection point pattern is positioned lower than a first and a second uppermost of the connection points 60c, 72b or than a third and a fourth bottommost lowermost of the connection points 60c, 72b in the height direction H.

The flexible printed circuit connection points 70d are positioned on a first portion 70c, 70c' of the flexible printed circuit 70, 70'. The first portion 70c, 70c' is positioned face-to-face with the converter circuit board second surface 72c, 72c'. The first portion 70c, 70c' extends into a main printed circuit 70a formed integrally with the FPC 70. The FPC 70 comprises a first fold 70b, 70b' towards the proximal end of the housing.

The main circuit board 70a extends in a direction away from the connection surface 60a of the camera module 60.

An outer maximum extent, i.e. a maximum outer diameter, in a cross-sectional direction of the tip part assembly is 2.9 mm. The cross-sectional direction extends at a right angle to the above-mentioned longitudinal direction L.

The converter circuit board 72, 72' further comprises at least one LED holder 72e, 72f for holding and/or supporting a light emitting diode, LED.

A first portion of the converter circuit board is positioned face-to-face with the connection surface 60a of the camera module 60, and a second portion of the converter circuit board comprising the LED holder 72e. This second portion extends from and away from this first portion in the lateral direction L and potentially beyond the connection surface 60a of the camera module 60. This lateral direction L extends transverse to the height direction H mentioned above.

A third portion of the converter circuit board comprises an LED holder 72f and extends from and away from the first portion of the converter circuit board in a lateral direction substantially opposite to the lateral direction L in which the second portion of the converter circuit board 72, 72' extends and potentially beyond the connection surface of the camera module. This opposite lateral direction similarly extends transverse to the height direction H.

Turning to FIG. 6, a bending section 4 is provided. The bending section 4 comprises a number of hingedly connected segments including a distal end segment 41, a proximal segment 43, and a plurality of intermediate segments 42 positioned between the distal end segment 41 and the proximal segment 43. The distal end segment 41 is adapted for being connected and/or attached to a housing of a tip part assembly, such as the housing 8 of FIGS. 4a-4c and 5a or the housing 8' of FIG. 5b, at a proximal end of the housing 8, 8'.

The following additional examples expand and further exemplify the features described above:

(1) A tip part assembly for an endoscope, comprising: a flexible printed circuit having two or more connection points, a camera module comprising a connection surface comprising two or more connection points for electrical communication of the camera module with the connection points of the flexible printed circuit, the connection points of the connection surface being arranged in a first connection point pattern, and a converter circuit board comprising a first surface and a second surface opposite the first surface, the first surface of the converter circuit board comprising connection points similarly arranged substantially in the first connection point pattern so that positions of the first surface connection points correspond to the connection surface connection points, the second surface of the converter circuit board comprising connection points arranged in a second connection point pattern, the second connection point pattern being different from the first connection point pattern, wherein the first surface connection points are connected to the connection surface connection points so that positions of the first surface connection points correspond to associated positions of the connection surface connection points, and wherein the second surface connection points are connected to the connection points of the flexible printed circuit.

(2) A tip part assembly according to (1), wherein the first connection point pattern and the second connection point pattern are different in one or more of the entries of the group consisting of: a total number of the contact points, a size of one or more of the contact points, a shape of one or more of the contact points, and a relative position between the contact points.

(3) A tip part assembly according to (1) or (2), wherein the connection surface of the camera module is a proximal end surface of the camera module, wherein the camera module comprises a distal end surface and a proximal end surface opposite the distal end surface and facing a proximal end of the endoscope.

(4) A tip part assembly according to any one of (1) to (3), wherein the flexible printed circuit comprises a surface comprising connection points arranged substantially in the second connection point pattern so that positions of the connection points of the second surface of the converter circuit board correspond to the flexible printed circuit surface connection points.

(5) A tip part assembly according to any one of (1) to (4), wherein the second connection point pattern extends shorter than the first connection point pattern in a height direction of the connection surface.

(6) A tip part assembly according to any one of (1) to (5) wherein the second connection point pattern is positioned lower than the first connection point pattern in a height direction of the connection surface.

(7) A tip part assembly according to any one of (1) to (6), wherein the first connection point pattern comprises four connection points arranged so that each connection point is positioned in a respective corner of a substantially rectangular shape, the second connection pattern comprising four connection points disposed on the second surface along a substantially straight line.

(8) A tip part assembly according to any one of (1) to (7), wherein the flexible printed circuit connection points are positioned on a first portion of the flexible printed circuit, the first portion being positioned face-to-face with the converter circuit board second surface, the first portion extending into a second portion of the flexible printed circuit, the second portion comprising a first fold towards the proximal end of the housing.

(9) A tip part assembly according to (8), wherein the tip part assembly further comprises a main circuit board connected to the flexible printed circuit second portion, the main circuit board extending in a direction away from the connection surface of the camera module.

(10) A tip part assembly according to any one of (1) to (9), further comprising a housing having a circumferentially extending outer surface for facing the environment, the outer surface enclosing a volume and extending in a longitudinal direction between a proximal end and a distal end of the housing, the working channel being at least partly housed in the housing and comprising an opening in a distal surface of the housing, the camera module being at least partly housed in the housing, at least a portion of the flexible printed circuit and at least a portion of the converter circuit board being arranged in the housing.

(11) A tip part assembly according to any one of (1) to (10), wherein an outer maximum extent in a cross sectional direction of the tip part assembly is less than 3.3 mm.

(12) A tip part assembly according to any one of (1) to (12), wherein the converter circuit board further comprises at least one LED holder for holding and/or supporting a light emitting diode, LED.

(13) A method of manufacture of a tip part assembly for an endoscope, the method comprising the steps of: providing a flexible printed circuit of the tip part assembly, the flexible printed circuit having two or more connection points, providing a camera module of the tip part assembly, the camera module comprising a connection surface comprising two or more connection points for electrical communication of the camera module with the connection points of the flexible printed circuit, the connection points of the connection surface being arranged in a first connection point pattern, and providing a converter circuit board of the tip part assembly, the converter circuit board comprising a first surface and a second surface opposite the first surface, the first surface of the converter circuit board comprising connection points similarly arranged substantially in the first connection point pattern so that positions of the first surface connection points correspond to the connection surface connection points, the second surface of the converter circuit board comprising connection points arranged in a second connection point pattern, the second connection point pattern being different from the first connection point pattern, connecting the first surface connection points to the connection surface connection points so that positions of the first surface connection points correspond to associated positions of the connection surface connection points; and connecting the second surface connection points to the connection points of the flexible printed circuit.

(14) A tip part assembly for an endoscope, the tip part assembly being manufactured according to (13).

(15) An endoscope comprising a tip part assembly according to any one of (1) to (12) or tip part assembly (14).

LIST OF REFERENCES

The following is a list of reference numerals used throughout this specification.
1 endoscope
11 monitor
12 cable socket
13 monitor cable
2 handle
21 control lever
3 insertion tube
3a proximal end
3b distal end
4 bending section
41 distal end segment
42 intermediate segment
43 proximal segment
5 tip part assembly
6 camera assembly
6' camera assembly
60 camera module
60a camera module connection surface
60b camera module top surface
60c camera module connection points
7 working channel
7a first working channel portion
7b second working channel portion
7c working channel distal opening
7d working channel chamfered portion
70 flexible printed circuit (FPC)
70' flexible printed circuit (FPC)
70a FPC second portion
70b FPC fold
70b' FPC fold
70c FPC first portion
70c' FPC first portion
70d FPC connection points
72 converter printed circuit
72' converter printed circuit
72a converter printed circuit first surface
72b first surface connection points
72c converter printed circuit second surface
72c' converter printed circuit second surface
72d second surface connection points
72e converter printed circuit second portion
72f converter printed circuit third portion
8 housing
8' housing
8a housing proximal end
8b housing distal end
8c outer surface
8d top volume
8e housing end wall
8e' housing end wall
8f window
8g circumferential wall
H height direction
L longitudinal direction
PD proximal-distal direction
T lateral direction

What is claimed is:

1. An endoscope comprising:
a tip part assembly including:
a housing having an inner surface;
a camera module positioned in the housing and having connection points in a first connection point pattern, the camera module having an upper surface adjacent the inner surface of the housing and a lower surface opposite the upper surface, a distance from the upper surface to the lower surface defining a height of the camera module;
a converter circuit board comprising a first surface and a second surface opposite the first surface, the first surface comprising connection points arranged in the first connection point pattern and electrically connected to the connection points of the camera module, and the second surface comprising connection points arranged in a second connection point pattern; and
a flexible circuit comprising a first portion positioned face-to-face with the converter circuit board and a second portion extending from the first portion and comprising a first fold extending toward a proximal end of the housing, the second portion not extending above a plane passing through the upper surface of the camera module, the flexible circuit further comprising connection points arranged in the first portion in the second connection point pattern and electrically connected to the connection points on the second surface of the converter circuit board.

2. The endoscope of claim 1, wherein the first connection point pattern and the second connection point pattern are different in one or more of the entries of the group consisting of: a total number of the contact points, a size of one or more of the contact points, a shape of one or more of the contact points, and a relative position between the contact points.

3. The endoscope of claim 1, wherein the camera module includes a proximal end surface extending between the upper surface and the lower surface, and the connection points are located on the proximal end surface.

4. The endoscope of claim 3, wherein the second connection point pattern extends shorter than the first connection point pattern in a height direction of the proximal end surface of the camera module.

5. The endoscope of claim 3, further comprising a working channel positioned at least partly in the housing, wherein the second connection point pattern is positioned closer to the working channel than the first connection point pattern.

6. The endoscope of claim 1, wherein all of the connection points in the second connection point pattern are aligned in one row and the connection points in the first connection point pattern are aligned in two rows.

7. The endoscope of claim 6, wherein the one row is more distant from the upper surface than the two rows.

8. The endoscope of claim 6, further comprising a working channel positioned in the housing, wherein the one row is closer to the working channel than the two rows.

9. The endoscope of claim 1, wherein the first connection point pattern consists of four connection points arranged in a respective corner of a substantially rectangular shape, and wherein the second connection pattern consists of four connection points arranged along a substantially straight line.

10. The endoscope of claim 1, wherein the second portion does not extend into an upper volume of the housing.

11. The endoscope of claim 1, wherein the second portion does not extend outside a camera module projection volume that extends proximally of the camera module.

12. The endoscope of claim 1, wherein the tip part assembly further comprises a main circuit board connected to the second portion of the flexible circuit and extending proximally of the first portion.

13. The endoscope of claim 1, wherein the housing has an outer surface facing the environment, the outer surface enclosing a volume and extending in a longitudinal direction between a proximal end and a distal end of the housing, a working channel being at least partly housed in the housing and comprising an opening in a distal surface of the housing, the camera module being at least partly housed in the housing, at least a portion of the flexible circuit and at least a portion of the converter circuit board being arranged in the housing.

14. The endoscope of claim 13, wherein an outer maximum extent in a cross sectional direction of the tip part assembly is less than 3.3 mm.

15. The endoscope of claim 1, further comprising a light emitting diode (LED), wherein the converter circuit board further comprises at least one LED holder supporting the LED, wherein the at least one LED holding portion extends laterally from the first surface and below the lower surface of the camera module, with a common plane extending between the first surface and the second surface and the at least one LED holding portion.

16. A method to manufacture the endoscope of claim 1, the method comprising:
    connecting the first surface connection points to the connection surface connection points of the camera module;
    connecting the second surface connection points to the connection points of the flexible printed circuit; and
    after connecting the first surface connection points and the second surface connection points, positioning the camera module in the housing.

17. The method of claim 16, further comprising securing the camera module and the flexible circuit in the housing without the flexible circuit extending above a plane passing through the upper surface of the camera module.

18. The endoscope of claim 1, wherein the first surface of the converter circuit board is entirely bound by edges, the second surface of the converter circuit board is entirely bound by edges, and none of the edges of the first surface and the second surface are coincident with each other.

19. The endoscope of claim 1, wherein the converter circuit board is devoid of a folded portion.

* * * * *